(12) United States Patent
Zchori-Fein et al.

(10) Patent No.: US 10,674,732 B2
(45) Date of Patent: Jun. 9, 2020

(54) ANTI-PHYTOPATHOGENIC COMPOSITIONS

(71) Applicant: The State of Israel, Ministry Of Agriculture & Rural Development, Agricultural Research Organization (ARO) (VOLCANI CENTER), Beit-Dagan (IL)

(72) Inventors: Einat Zchori-Fein, Shekhanya (IL); Vered Naor, Katzrin (IL); Lilach Iasur-Kruh, Kiryat-Motzkin (IL); Tirtza Zahavi, Kibbutz Geshur (IL); Netta Mozes-Daube, Moshava Yokneam (IL)

(73) Assignee: The State of Israel, Ministry of Agriculture & Rural Development Agricultural Research Organization, Beit-Dagan (IL)

( * ) Notice: Subject to any disclaimer, the term of this patent is extended or adjusted under 35 U.S.C. 154(b) by 0 days.

(21) Appl. No.: 15/569,875

(22) PCT Filed: Apr. 26, 2016

(86) PCT No.: PCT/IL2016/050438
§ 371 (c)(1),
(2) Date: Oct. 27, 2017

(87) PCT Pub. No.: WO2016/174673
PCT Pub. Date: Nov. 3, 2016

(65) Prior Publication Data
US 2018/0206504 A1 Jul. 26, 2018

Related U.S. Application Data

(60) Provisional application No. 62/154,246, filed on Apr. 29, 2015.

(51) Int. Cl.
*A01N 25/00* (2006.01)
*A01N 63/00* (2020.01)
*A01N 63/10* (2020.01)
*C12N 1/20* (2006.01)
*A01N 37/46* (2006.01)
*A01N 43/42* (2006.01)
*A01N 25/30* (2006.01)
*A01N 25/24* (2006.01)

(52) U.S. Cl.
CPC ............ *A01N 63/10* (2020.01); *A01N 37/46* (2013.01); *A01N 43/42* (2013.01); *A01N 63/00* (2013.01); *C12N 1/20* (2013.01); *A01N 25/24* (2013.01); *A01N 25/30* (2013.01); *A01N 2300/00* (2013.01)

(58) Field of Classification Search
CPC ......... A01N 25/30; A01N 63/04; A01N 25/04
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,563,459 A * | 1/1986 | Grohe | A01N 43/42 514/187 |
| 4,666,828 A | 5/1987 | Gusella | |
| 4,683,202 A | 7/1987 | Mullis | |
| 4,801,531 A | 1/1989 | Frossard | |
| 4,879,219 A | 11/1989 | Wands et al. | |
| 4,895,803 A * | 1/1990 | Hubner | A61L 2/0088 435/383 |
| 5,011,771 A | 4/1991 | Bellet et al. | |
| 5,192,659 A | 3/1993 | Simons | |
| 5,240,940 A * | 8/1993 | Arnold | A01N 43/42 514/228.8 |
| 5,272,057 A | 12/1993 | Smulson et al. | |
| 5,281,521 A | 1/1994 | Trojanowski et al. | |

(Continued)

FOREIGN PATENT DOCUMENTS

EP 2343280 A1 * 7/2011
JP 38005684 * 3/1960
(Continued)

OTHER PUBLICATIONS

Isleib et al., 2012; Michigan State University Extension, pp. 1-4 (Year: 2012).*

(Continued)

*Primary Examiner* — Gary B Nickol
*Assistant Examiner* — Lakia J Jackson-Tongue
(74) *Attorney, Agent, or Firm* — The Roy Gross Law Firm, LLC; Roy Gross

(57) ABSTRACT

The present invention relates to an isolated bacterium and composition comprising same having anti-pathogenic activity. The invention further relates to compounds derived from said bacterium or analogs thereof, and methods of using same for treating or reducing the symptoms of a pathogen including but not limited to a phytopathogen.

4 Claims, 14 Drawing Sheets
Specification includes a Sequence Listing.

(56) References Cited

U.S. PATENT DOCUMENTS

| | | | | |
|---|---|---|---|---|
| 6,417,195 | B1* | 7/2002 | Lebl | C07D 217/26 |
| | | | | 506/15 |
| 9,586,969 | B2* | 3/2017 | Bou Hamdan | C07D 487/04 |
| 2010/0113513 | A1* | 5/2010 | Murphy Kessabi | A01N 43/42 |
| | | | | 514/311 |
| 2011/0319430 | A1* | 12/2011 | Long | C07D 231/12 |
| | | | | 514/256 |

FOREIGN PATENT DOCUMENTS

| | | | |
|---|---|---|---|
| WO | WO 86/06630 | * | 11/1986 |
| WO | WO 2003080596 | * | 2/2003 |
| WO | 2005034857 A2 | | 4/2005 |

OTHER PUBLICATIONS

Plant Natural research center, https://www.planetnatural.com/pest-problem-solver/plant-disease/common-rust/, accessed on Mar. 15, 2019 (Year: 2019).*

Uttarwar et al., Journal of Chemical and Pharmaceutical Research, 2013; 5(4): 41-46 (Year: 2013).*

Cho. et al, "Antimicrobial Activity of Quinoline Derivatives Isolated from Ruta chalepensis Toward Human Intestinal Bacteria" Journal of Microbiology and Biotechnology, Jun. 2005, vol. 15 No. 3, pp. 646-651.

Marzorati M. et al, "A novel Bacteroidetes symbiont is localized in Scaphoideus titanus, the insect vector of Flavescence dorée in Vitis vinifera", Applied and Environmental Microbiology, Feb. 2006, vol. 72 No. 2, pp. 1467-1475.

Fitch et al., "Optimal sequence alignments", Proc. Nati Acad. Sci. USA, vol. 80, pp. 1382-1386, Mar. 1983.

Needleman et al., "A General Method Applicable to the Search for Similarities in the Amino Acid Sequence of Two Proteins", J. Mol. Biol. (1970) 48, 443-453.

Karlin et al., "Applications and statistics for multiple high-scoring segments in molecular sequences", Proc. Natl. Acad. Sci. USA, vol. 90, pp. 5873-5877, Jun. 1993.

Altschul et al., "Basic Local Alignment Search Tool", J. Mol. Biol. (1990) 215, 403-410.

Altschul et al., "Gapped BLAST and PSI-BLAST: a new generation of protein database search programs", Nucleic Acids Research, 1997, vol. 25, No. 17 3389-3402.

Jung et al., "*Dyella ginsengisoli* sp. nov., isolated from soil of a ginseng field in South Korea", International Journal of Systematic and Evolutionary Microbiology, 2009, 59, 460-465.

Li et al., "Isolation and characteristics of a novel biphenyl-degrading bacterial strain, Dyella ginsengisoli LA-4", Journal of Environmental Sciences 21, 2009, 211-217.

* cited by examiner

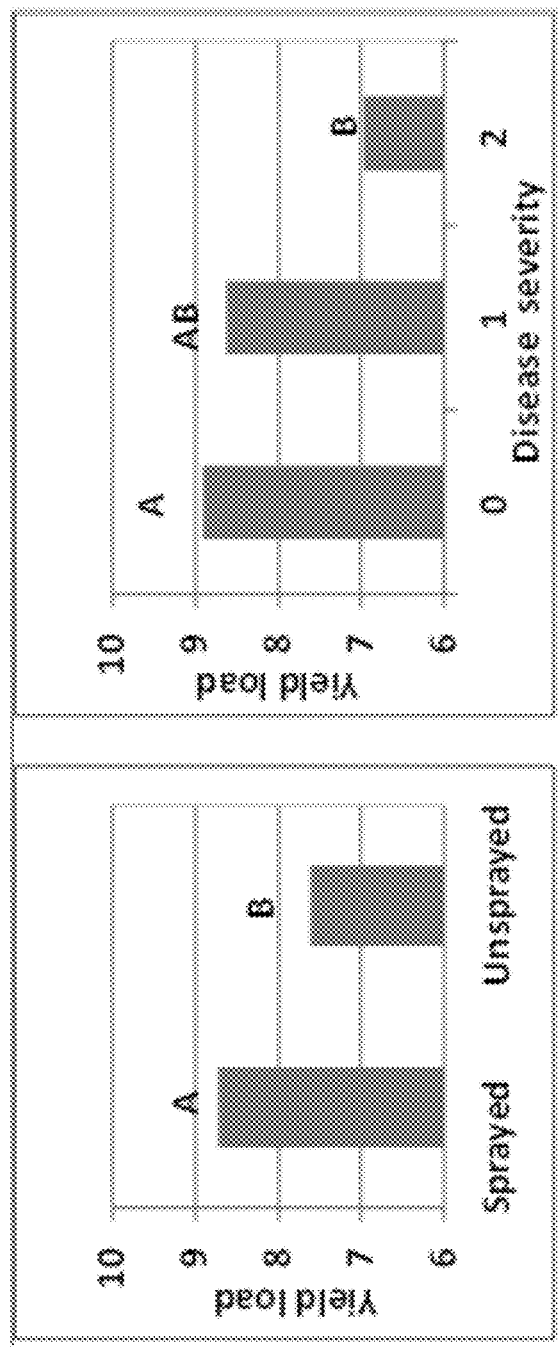
Figure 8A
Figure 8B
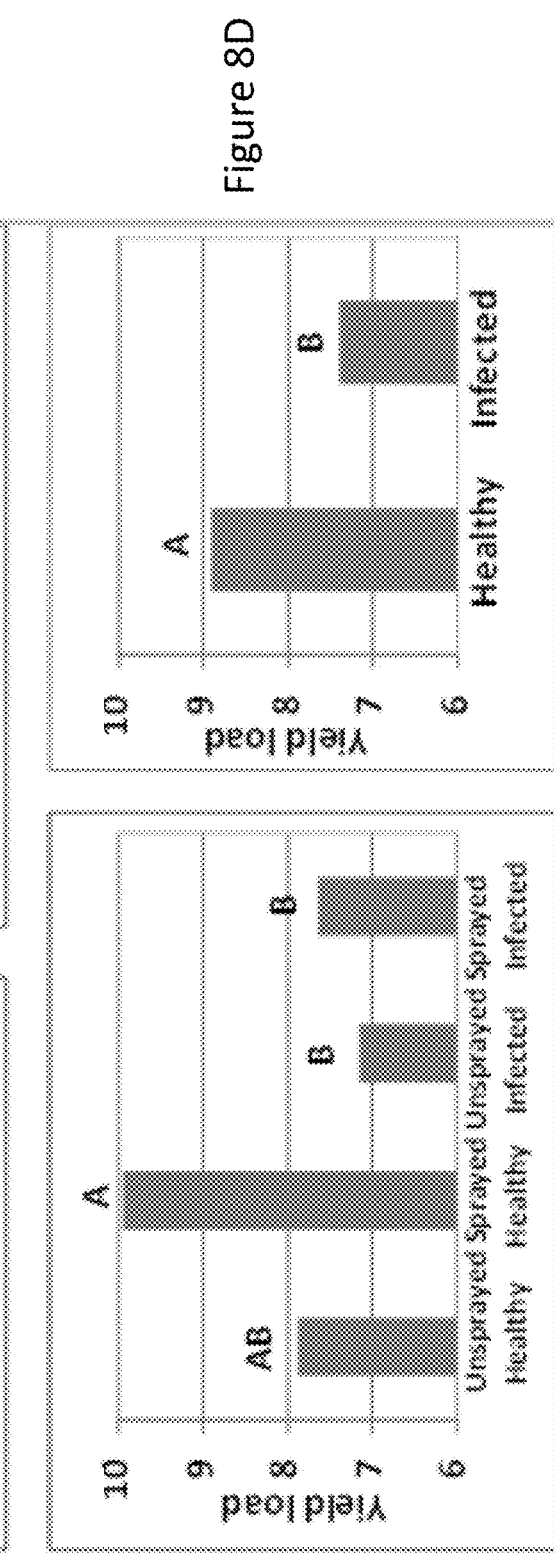
Figure 8C
Figure 8D

ANTI-PHYTOPATHOGENIC COMPOSITIONS

RELATED APPLICATIONS

This application is a National Phase of PCT Patent Application No. PCT/IL2016/050438 having International filing date of Apr. 26, 2016, which claims the benefit of priority of U.S. Patent Application No. 62/154,246 filed on Apr. 29, 2015. The contents of the above applications are all incorporated by reference as if fully set forth herein in their entirety.

FIELD OF THE INVENTION

The present invention, in some embodiments thereof, relates to anti-phytophathogenic compositions.

BACKGROUND OF THE INVENTION

The bacterial genus *Ca. Phytoplasma* consists of relatively small bacteria, all of which are phloem-limited, non-helical and wall-less plant pathogens. Unlike viruses, phytoplasmas have their own, highly reduced metabolism although some of the molecules essential for their survival are acquired from the host. They represent a monophyletic Glade within the class Mollicutes, which is currently divided into at least 15 subgroups on the basis of sequence analyses of various conserved genes.

Grapevine yellows (GY), a complex of diseases that were originally thought to be caused by viruses, are now known to have a phytoplasma etiology. Almost identical symptoms of the GY syndrome are caused by different phytoplasmas and appear on leaves, shoots and clusters of grapevines (*Vitis vinifera*). Typical symptoms include discoloration and necrosis of leaf veins and leaf blades, downward curling of leaves, lack or incomplete lignifications of shoots, stunting and necrosis of shoots, abortion of inflorescences and shriveling of berries. Those symptoms are related to callose deposition at the sieve plates and subsequent degeneration of the phloem. Although no resistant cultivars of *V. vinifera* or rootstocks are known so far, the various grape varieties differ considerably as far as symptom severity is concerned. It ranges from fast decline and death in highly susceptible cultivars to tolerant rootstocks as symptomless carriers of the pathogen.

Approximately 70% of world grape production is used for wine, which is the highest value-added agri-food product in the world. The primary factor influencing wine quality is the condition under which the grapes are grown. Diseases, pests and viticultural practices greatly impact the consistency of the grape production and quality. Most of the time, diseases and pests are controlled with pesticides, either preventively or responsively.

The control of pathogens including but not limited to phloem-restricted pathogens (e.g., phytoplasma) needs new strategies given that conventional application were proven inefficient.

SUMMARY OF THE INVENTION

The present invention relates to an isolated bacterium and composition comprising same having anti-pathogenic activity. The invention further relates to compounds derived from said bacterium or analogs thereof, and methods of using same for treating or reducing the symptoms of a pathogen, including but not limited to, a phytopathogen.

According to one aspect, there is provided an isolated bacterium comprising a nucleic acid sequence having at least 98% sequence identity to: SEQ ID NO: 1 and at least one additional nucleic acid sequence having at least 85% sequence identity to any one of SEQ ID NO: 2-14.

According to some embodiments, the isolated bacterium comprises the nucleic acid sequences as set forth in SEQ ID NO: 2-14. According to some embodiments, the isolated bacterium comprises a nucleic acid sequence having at least 10% sequence variety to: *Dyella ginsengisoli*.

According to another aspect, there is provided a composition comprising the isolated bacterium of the invention and any one of an emulsifier, a growth substrate or their combination.

According to some embodiments, the composition comprises an emulsifier comprising a material selected from the group consisting of: non-ionic surfactant, anionic surfactant, cationic surfactant or an amphiphilic surfactant. According to some embodiments, the emulsifier is a non-ionic surfactant. In one embodiment, said non-ionic surfactant comprises polyoxyethylene (20) sorbitan monolaurate.

According to some embodiments, the composition comprises a growth substrate, said growth substrate comprises a selective bacterial growth medium. According to some embodiments, said selective bacterial growth medium comprises one or more materials selected from the group consisting of a sugar and an amino acid. According to some embodiments, said sugar is selected from the group consisting of: arabinose, mannose, sucrose, melibiose, galactose, inositol, glucoside, and any combination or derivative thereof. According to some embodiments, said amino acid is selected from the group consisting of: proline nitroanilide, γ-L-glutamyl p-nitroanilide, phenylalanine, glycine, arginine, and any combination thereof.

According to some embodiments, the composition further comprising one or more compounds selected from the group consisting of: Quinolinecarboxaldehyde, and Hydroxymethyl-2-furaldehyde, or any derivative thereof.

According to another aspect, there is comprises a composition comprising Quinolinecarboxaldehyde and Hydroxymethyl-2-furaldehyde, or any derivatives thereof.

According to some embodiments, the composition of the invention further comprising a material selected from the group consisting of: a fertilizer, a herbicide, a pesticide, or any combination thereof.

According to another aspect, there is provided a method of treating or reducing the symptoms of a pathogen, the method comprising the step of contacting said pathogen with the isolated bacterium or the composition disclosed herein, thereby treating or reducing the symptoms of the pathogen.

According to some embodiments, said pathogen is a phytopathogen. According to some embodiments, the phytopathogen is selected from *Xanthomonas campestris*, *Candidatus* Liberibacte and phytoplasma. According to some embodiments, the phytopathogen is phytoplasma. In another exemplary embodiment, the pathogen is *Ca. Liberibacter*. In another exemplary embodiment, the pathogen is *Xanthomonas campestris*.

According to some embodiments, the pathogen is *Spiroplasma melliferum*.

According to some embodiments, there is provided a composition comprising a plant seed and a capsule encapsulating said plant seed, wherein said capsule comprises:
i. the bacterium or composition disclosed herein, and
ii. a biocompatible material.

According to some embodiments, the biocompatible material comprises an adhesive material. According to some embodiments, said adhesive material is selected from the group consisting of: guar, derivatized guar, polyacrylamide, poly(methacrylic acid), poly(acrylic acid), polyacrylate, poly(ethylene glycol), phosphonate-end capped polymers, polyethyleneoxide, poly(vinyl alcohol), polyglycerol, polytetrahydrofuran, polyamide, starch, derivatized starch, waxy maize, sorghum, waxy sarghum, sago, dextrin, chitin, chitosan, alginate compositions, gum, pectin, cellulose, or any combination or derivative thereof.

According to some embodiments, said biocompatible material is or comprises a mineral. According to some embodiments, the composition further comprising a binder. According to some embodiments, the binder is selected from the group consisting of: gelatin, polyvinyl acetate, polyvinylpyrolidones, dextrin, malto-dextrins, polysaccharides, fats, oils, proteins, shellacs, vinylidene chloride, vinylidene chloride copolymers, calcium lignosulfonates, acrylic copolymer, polyvinylacrylate, zein, chitosan, polyethylene oxide, acrylimide polymer, polyhydroxyethyl acrylate, a methylacrylimide monomer, alginate, polychloroprene, syrup, or any combination thereof.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 4A: General Bacteria—shown as gray sections; FIG. 4B: DLB-specific; FIG. 4C: Visible light; FIG. 4D: all images combined.

FIG. 5A: healthy; FIG. 5B: healthy inoculated with DLB; FIG. 5C: phytoplasma-infected; FIG. 5D: phytoplasma-infected inoculated with *Dyella*. FIG. 5E depicts the influence of DLB on grapevine plantlets eight weeks post inoculation of healthy ("H") and phytoplasma-infected ("Phyto") plants with ("+D") and without DLB.

FIG. 6A: healthy; FIG. 6B: healthy inoculated with DLB; FIG. 6C: phytoplasma-infected; FIG. 6D: phytoplasma-infected inoculated with DLB. FIG. 6E demonstrates the influence of DLB on periwinkle plantlets eight weeks post inoculation of healthy ("H") and phytoplasma-infected ("Phyto") plants with ("+D") and without DLB (left panel: shoot length, right panel: dry weight).

FIGS. 8A-D present bar graphs showing the influence of DLB application on grapevines.

DETAILED DESCRIPTION OF THE INVENTION

Figure 1:
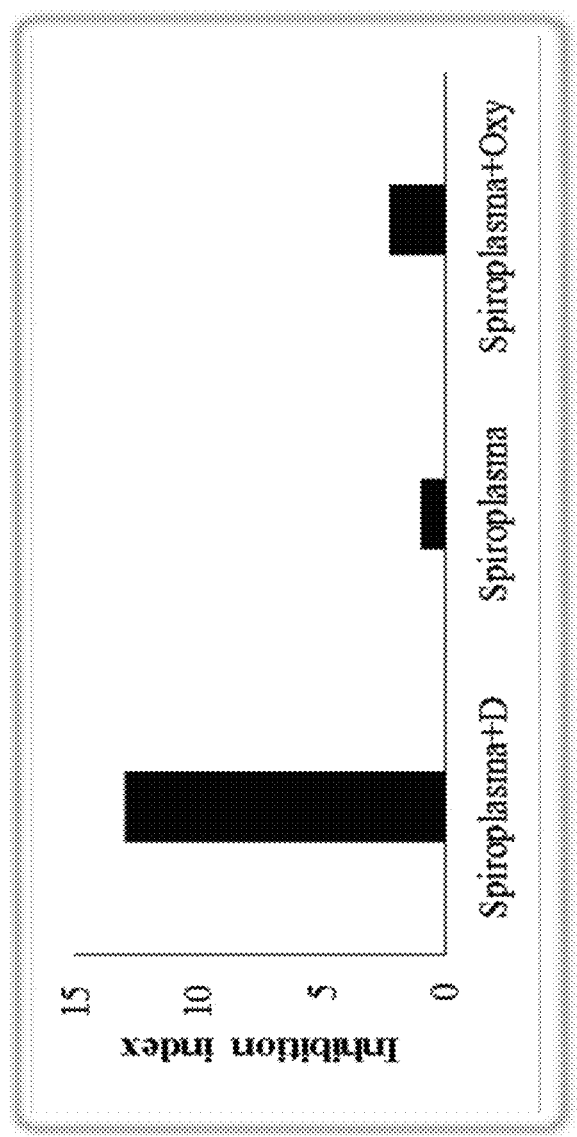
FIG. 1 illustrates the inhibition of the *Dyella*-like bacterium filtrate (depicted "D") on in vitro development of *Spiroplasma melliferum* in comparison to inhibition of 0.5 µg/ml Oxytetracycline (depicted "Oxy").

The present invention, in some embodiments thereof, relates to a novel bacterium, compositions comprising same. The invention further relates to compositions comprising compounds derived from said bacterium or synthetic analogs thereof. The inventions further relates to methods of use thereof, such as for treating or preventing crop diseases, including, but not limited to crop diseases caused by phytoplasma.

The present invention present for the first time a novel bacterium, referred to herein as "*Dyella*-like bacterium" or "DLB", with a specific inhibitory effect on the symptoms of phloem-restricted pathogens such as phytoplasma. Furthermore, the bacterium of the invention is advantageously able to penetrate the treated plants, via both the plant's roots, seeds and leaves. The present invention further demonstrate the utility of the bacterium disclosed herein in a *Xanthomonas* pathogenesis assay, indicating that the bacterium also reduces the damage of pathogenic bacteria which is not only restricted to the phloem.

According to some embodiments, the present invention provides an isolated bacterium comprising a nucleic acid sequence having at least 98% sequence identity to the nucleic acid sequence as set forth in SEQ ID NO: 1. In some embodiments, by "having at least 98% identity to the nucleic acid sequence as set forth in SEQ ID NO: 1" it is further meant to refer to at least 98.5%, at least 99%, at least 99.1%, at least 99.5%, or at least 99.9%, or 100% sequence identity to the nucleic acid sequence as set forth in SEQ ID NO: 1, including any value or range therebetween.

In some embodiments, the isolated bacterium further comprises a nucleic acid sequence having at least 85% sequence identity to any one of SEQ ID NO: 2-14. In some embodiments, the isolated bacterium further comprises a plurality of nucleic acid sequences having at least 85% sequence identity to any one of SEQ ID NO: 2-14. A "plurality" as used herein, refers to at least 2, at least 3, at least 4, at least 5, at least 6, at least 7, at least 8, at least 9, at least 10, at least 11, at least 12, at least 13 polynucleotide sequences as set forth in SEQ ID NO: 2-14. Each possibility represents a separate embodiment of the present invention.

In some embodiments, the isolated bacterium comprises a nucleic acid sequence having at least 85%, at least 90%, at least 95%, at least 99% sequence identity to any one of SEQ ID NO: 2. In some embodiments, the isolated bacterium comprises a nucleic acid sequence comprising SEQ ID NO: 2.

In some embodiments, the isolated bacterium comprises a nucleic acid sequence having at least 85%, at least 90%, at least 95%, at least 99% sequence identity to any one of SEQ ID NO: 3. In some embodiments, the isolated bacterium comprises a nucleic acid sequence comprising SEQ ID NO: 3.

In some embodiments, the isolated bacterium comprises a nucleic acid sequence having at least 85%, at least 90%, at least 95%, at least 99% sequence identity to any one of SEQ ID NO: 4. In some embodiments, the isolated bacterium comprises a nucleic acid sequence comprising SEQ ID NO: 4.

In some embodiments, the isolated bacterium comprises a nucleic acid sequence having at least 85%, at least 90%, at least 95%, at least 99% sequence identity to any one of SEQ ID NO: 5. In some embodiments, the isolated bacterium comprises a nucleic acid sequence comprising SEQ ID NO: 5.

In some embodiments, the isolated bacterium comprises a nucleic acid sequence having at least 85%, at least 90%, at least 95%, at least 99% sequence identity to any one of SEQ ID NO: 6. In some embodiments, the isolated bacterium comprises a nucleic acid sequence comprising SEQ ID NO: 6.

In some embodiments, the isolated bacterium comprises a nucleic acid sequence having at least 85%, at least 90%, at least 95%, at least 99% sequence identity to any one of SEQ ID NO: 7. In some embodiments, the isolated bacterium comprises a nucleic acid sequence comprising SEQ ID NO: 7.

In some embodiments, the isolated bacterium comprises a nucleic acid sequence having at least 85%, at least 90%, at least 95%, at least 99% sequence identity to any one of SEQ ID NO: 8. In some embodiments, the isolated bacterium comprises a nucleic acid sequence comprising SEQ ID NO: 8.

In some embodiments, the isolated bacterium comprises a nucleic acid sequence having at least 85%, at least 90%, at least 95%, at least 99% sequence identity to any one of SEQ ID NO: 9. In some embodiments, the isolated bacterium comprises a nucleic acid sequence comprising SEQ ID NO: 9.

In some embodiments, the isolated bacterium comprises a nucleic acid sequence having at least 85%, at least 90%, at least 95%, at least 99% sequence identity to any one of SEQ ID NO: 10. In some embodiments, the isolated bacterium comprises a nucleic acid sequence comprising SEQ ID NO: 10.

In some embodiments, the isolated bacterium comprises a nucleic acid sequence having at least 85%, at least 90%, at least 95%, at least 99% sequence identity to any one of SEQ ID NO: 11. In some embodiments, the isolated bacterium comprises a nucleic acid sequence comprising SEQ ID NO: 11.

In some embodiments, the isolated bacterium comprises a nucleic acid sequence having at least 85%, at least 90%, at least 95%, at least 99% sequence identity to any one of SEQ ID NO: 12. In some embodiments, the isolated bacterium comprises a nucleic acid sequence comprising SEQ ID NO: 12.

In some embodiments, the isolated bacterium comprises a nucleic acid sequence having at least 85%, at least 90%, at least 95%, at least 99% sequence identity to any one of SEQ ID NO: 13. In some embodiments, the isolated bacterium comprises a nucleic acid sequence comprising SEQ ID NO: 13.

In some embodiments, the isolated bacterium comprises a nucleic acid sequence having at least 85%, at least 90%, at least 95%, at least 99% sequence identity to any one of SEQ ID NO: 14. In some embodiments, the isolated bacterium comprises a nucleic acid sequence comprising SEQ ID NO: 14.

In some embodiments, the isolated bacterium further comprises a nucleic acid sequence having at least 10%, at least 15%, at least 20% sequence variety to: *Dyella ginsengisoli*. In some embodiments, the isolated bacterium further comprises a nucleic acid sequence having at least 10%, at least 15%, at least 20% sequence variety to: *Frateuria aurantia*.

It is appreciated that one skilled in the art is aware of determining the *Dyella ginsengisoli* or *Frateuria aurantia* polynucleotide sequence (see, Jung et al. Int J Syst Evol Microbiol. 2009; 460-5; and Li et al. J Environ Sci, 2009; 21(2):211-7) and thus determining the sequence variety of the bacterium of the invention as opposed to the *Dyella ginsengisoli* or *Frateuria aurantia* bacterium. In specific embodiments, the 16S rRNA gene of the bacterium of the invention has 97% sequence identity to the 16S rRNA gene of *Dyella ginsengisoli* (accession No. EF191353; SEQ ID NO: 15).

In specific embodiments, the ITS sequence of the bacterium of the invention has about 84% sequence identity to the ITS sequence of *Frateuria aurantia* (accession No. CP003350).

In some embodiments, by "having at least 85% identity" to a referenced nucleic acid sequence it is further meant to refer to at least 90%, at least 91%, at least 92%, at least 93%, or at least 94%, at least 95%, at least 96%, at least 97%, at least 98%, at least 99%, or at least 100% sequence identity to the referenced nucleic acid sequence, including any value or range therebetween.

As described hereinbelow, SEQ ID NO: 1 may be detected using the primer pair having the nucleic acid sequence as set forth in SEQ ID NO: 16-17 or the probe sequence having the nucleic acid sequence as set forth in SEQ ID NO: 18-19. As further described hereinbelow, SEQ ID NO: 2 may be detected using the primer pair having the nucleic acid sequence as set forth in SEQ ID NO: 16-17. A skilled artisan will appreciate that the primers and probes are provided herein as a non-limiting example for detecting the 16S rRNA (SEQ ID NO: 1) and internal transcribed spacer (ITS) sequence (SEQ ID NO: 2), respectively, of the bacterium of the present invention.

In particular embodiments, the bacterium of the invention is in a form of a biologically pure culture. As used herein the phrase "biologically pure culture" refers to a culture of the bacteria, wherein at least 80% (e.g., at least 85%, 90%, 95%, or even all 100%) of the microorganisms in the culture and/or in the composition are of these bacteria.

In some embodiments, a biologically pure culture is also referred to as "an isolate". The term "isolate" is intended to specifically refer to an organism that is removed from its original source and purified from additional components with which it was originally associated, and thus is altered by the hand of man from its natural environment. It should be noted that the composition may include whole bacterial cells, parts thereof and extracts therefrom. Isolated bacterium refers to a bacterium that is e.g., cultivated, purified and/or cultured separately from the environment in which it is naturally located. Isolated material further encompasses bacterium isolated and cultured separately from the environment in which it was located, where these isolates are present in purified compositions that do not contain any significant amount of other microorganisms such as other bacterial strains. An "isolated bacterium" as used herein does not include the bacterium as it exists in its natural environment prior to isolation and/or substantial purification.

In some embodiments, said isolated bacteria are isolated from the natural environment, such as from the plant hopper *Hyalesthes obsoletus* (Hemiptera: Cixiidae), by steps known in the art. As demonstrated herein below, the bacterium disclosed herein is a Gram negative, aerobic, rod shaped bacterium that belongs to the family Xanthomonadaceae (in which no spore forming species has been reported).

As used herein, the term "genome" refers to the total genetic information or hereditary material possessed by an organism, e.g., the entire genetic complement of a bacteriume. A genome can comprise RNA or DNA. Typically, a bacterial genome is circular.

As used herein, the term "nucleic acid" is well known in the art. A "nucleic acid" as used herein will generally refer to a molecule (e.g., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C).

As used herein, the expressions "nucleotide sequence", "nucleic acid sequence," "polynucleotide sequence", and equivalent or similar phrases refer to the order of nucleotide monomers in the nucleotide polymer. By convention, a nucleotide sequence is typically written in the 5' to 3' direction. A polynucleotide may be a polymer of RNA or DNA that is single- or double-stranded, that optionally contains synthetic, non-natural or altered nucleotide bases. Unless otherwise indicated, a particular polynucleotide sequence of the invention optionally encompasses complementary sequences, in addition to the sequence explicitly indicated. As used herein, it is not intended that the term "polynucleotide" be limited to naturally occurring polynucleotide structures, naturally occurring nucleotides sequences, naturally occurring backbones or naturally occurring internucleotide linkages. One skilled in the art knows well the wide variety of polynucleotide analogues, unnatural nucleotides, non-natural phosphodiester bond linkages and internucleotide analogs that find use with the invention.

The present invention further provides variants and analogs off the disclosed bacterium. The term "variant" of a reference bacterium designates bacterium having variation(s) in the genomic sequence and/or polypeptide(s) encoded thereby as compared to the reference bacterium, while retaining the same phenotypic characteristic as the reference bacterium. Variants also encompass bacterium having variation(s) in the genomic sequence and/or polypeptide(s) encoded thereby as compared to the reference bacterium, while improving the phenotypic characteristic as the reference bacterium. In some embodiments, the variants of the invention are genetically engineered variants (e.g., a result of genetically engineered mutation(s) to the nucleic acid sequence of the reference bacterium).

Variants may comprise e.g., silent mutations, conservative mutations, minor deletions, and/or minor replications of genetic material, and retain phenotypic characteristics of the reference bacterium. In some embodiments, the variant of the invention retain any observable characteristic or property that is dependent upon the genome of the bacterium of the invention, such as phenotypic characteristics of the bacterium and/or inhibitory activity against phytoplasma.

The term "phenotypic characteristic" designates the morphology and/or host-range of a bacterium. Methods for phenotyping bacterium are well known in the art.

According to some embodiments, the invention further encompasses variants having a genome comprising at least 85%, 86%, 87%, 88%, 89%, 90%, 91%, 92%, 93%, 94%, 95%, 96%, 97%, 98% or 99% sequence identity to the nucleic acid sequences as set forth in SEQ ID NO: 2-14. Each possibility represents a separate embodiment of the present invention. According to some embodiments, the invention further encompasses variants having a genome comprising at least 1, at least 2, at least 4, at least 5 or at least 10 mutations relative to the nucleic acid sequences as set forth in SEQ ID NO: 2-14.

In some embodiments, the mutations include deletions, insertions, substitutions or any combination thereof. In some embodiments, the deletions, insertions, substitutions may be found in a non-coding region such as operon, and promoter regions. In some embodiments, the deletions, insertions, substitutions may be found in a coding region of the bacterium. In some embodiments, the deletions, insertions, substitutions are silent mutation which do not result in changes of the coded amino acid sequence.

The term "% identity" in relation to nucleic acid sequences designates the level of identity or homology between the sequences and may be determined by techniques known in the art. The term "% variety" in relation to nucleic acid sequences designates the level of variety between the sequences and may be determined by techniques known in the art Percentage sequence identity can be determined, for example, by the Fitch et al. version of the algorithm (Fitch et al, Proc. Natl. Acad. Sci. U.S.A. 80:1382-1386 (1983)) described by Needleman et al, (Needleman et al, J. Mol. Biol. 48:443-453 (1970)), after aligning the sequences to provide for maximum homology. Alternatively, the determination of percent identity between two sequences can be accomplished using the mathematical algorithm of Karlin and Altschul (1993) Proc. Natl. Acad. Sci. USA 90:5873-5877. Such an algorithm is incorporated into the BLASTP program of Altschul et al. (1990) J. Mol. Biol. 215, 403-410. In order to obtain gapped alignments for comparative purposes, Gapped BLAST is utilized as described in Altschul et al (1997) Nucleic Acids Res. 25:3389-3402. When utilizing BLAST and Gapped BLAST programs, the default parameters of the respective programs (e.g.,) (BLAST) are used.

The variants may be made to specific bacteriophages by chemical, radiological or other methods well known to those skilled in the art. The variants may also be made by homologous recombination methods well known to those skilled in the art. The variants having a mutated sequence may comprise deletions, insertions additions or substitutions, all of which may be constructed by routine techniques.

Bacterium Compositions

In some embodiments, the present invention provides a composition (referred to hereinthroughout as: "bacterium composition") comprising the bacterium of the invention, i.e., the *Dyella*-like bacterium.

(i) Emulsifiers

In some embodiments, the bacterium composition further comprises an emulsifier. The term "emulsifier", as used herein, refers to a substance which promotes the formation and stabilization of an emulsion. According to some embodiments, the emulsifier is selected from the group consisting of sodium dodecyl sulfate, a phospholipid, a glycolipid, a triglyceride, lecithin, soap, sodium stearate, potassium stearate, ammonium stearate, sodium oleate, potassium oleate, ammonium oleate, sodium palmitate, potassium palmitate and ammonium palmitate.

In one embodiment, the emulsifier is a surfactant. The term "surfactant" (also known as surface-active agent) includes any agent that lowers the surface tension (or interfacial tension) between two liquids or between a liquid and a solid or between gas and liquid. Surfactants may act as detergents, wetting agents, emulsifiers, foaming agents, and/or dispersants.

Typically, surfactant includes any nonionic, anionic, cationic, zwitterionic, and amphoteric acceptable surfactant. In some embodiments, the emulsifier is a non-ionic surfactant. In some embodiments, the emulsifier is an anionic surfactant. In some embodiments, the emulsifier is a cationic surfactant. In some embodiments, the emulsifier is an amphiphilic surfactant. According to some embodiments of the invention, the emulsifier is selected from the group consisting of cationic emulsifier, an anionic emulsifier, a non-ionic emulsifier and combinations thereof.

Nonionic surfactants include, but are not limited to, sorbitan fatty acid esters, polyoxysorbitan fatty acid esters, polyoxyalkylene higher alcohol ethers, and polyoxyalkylene higher alcohol esters. Non-limiting examples of nonionic surfactants include polyoxyethylene sorbitol esters such as polysorbate 80 (TWEEN® 80), polysorbate 60 (TWEEN® 60) and polysorbate 20 (TWEEN® 20), Tyloxapol; polyoxyethylene isooctylphenyl ethers such as Triton X-100, polyoxyethylene nonylphenyl ethers such as NP-40, polyoxyethylene dodecyl ethers such as Brij 58, octyl glucoside, and alkyl maltoside such as n-dodecyl-beta-D-maltoside; Poloxamer 4070; Poloxamer 188; and polyoxyl 40 stearate. Each possibility is a separate embodiment of the invention.

Nonionic surfactants include, but are not limited to, sorbitan fatty acid esters, polyoxysorbitan fatty acid esters, polyoxyalkylene higher alcohol ethers, and polyoxyalkylene higher alcohol esters. Non-limiting examples of nonionic surfactants include polyoxyethylene sorbitol esters such as polysorbate 80, polysorbate 60 and polysorbate 20, Tyloxapol; polyoxyethylene isooctylphenyl ethers such as Triton X-100® which has nonionic surfactant that has a hydrophilic polyethylene oxide chain, polyoxyethylene nonylphenyl ethers such as nonyl phenoxypolyethoxylethanol, polyoxyethylene dodecyl ethers such as Brij®58 with CAS Registry Number 9004-95-9, octyl glucoside, and alkyl maltoside such as n-dodecyl-beta-D-maltoside; Poloxamer 4070; Poloxamer 188; and polyoxyl 40 stearate. Each possibility is a separate embodiment of the invention.

Anionic surfactants include, but are not limited to, alkyl sulfates, olefin sulfates, ether sulfates, monoglyceride sulfates, alkyl sulfonates, aryl sulfonates, olefin sulfonates, alkyl sulfosuccinates, aryl sulfosuccinates, including sodium dodecyl sulphate (SDS), dioctyl sodium sulfosuccinate, dioctyl sodium sulfonate. Each possibility represents a separate embodiment of the invention.

Cationic surfactants include, but are not limited to, benzalkonium salts, polyoxyalkylene alkylamines, alkylamines, alkanolamine fatty acid esters, quaternary ammonium fatty acid esters, dialkyl ammonium salts, alkyl pyridinium salts including stearylamine, triethanolamine oleate, benzethonium chloride. Each possibility is a separate embodiment of the invention.

Amphoteric surfactants include, for example, imidazoline-based amphoteric surfactants (such as a 2-cocoyl-2-imidazoliniumhydroxide-1-carboxyethyloxy-2-sodium salt), betaine-based surfactants (such as alkyl betaine, amide betaine, and sulfo betaine), and acylmethyl taurine. Each possibility is a separate embodiment of the invention.

The surfactant is present in the composition of the present invention in an amount of from about 0.001% to about 10% by weight of the total weight of the composition, alternatively in an amount of from about 0.001% to about 0.5% by weight, or in an amount of from about 0.001% to about 0.2% by weight, or in an amount of from about 0.001% to about 0.05% by weight of the total weight of the composition.

The emulsion, in some embodiments, is provided by preparing and mixing two solutions, one being the aqueous phase (water-based phase) and another being the organic phase (oil-based phase), so as to disperse one phase in the other.

(ii) Growth Substrate

In some embodiments, the composition of the invention comprises the bacterium described herein and a growth substrate. In some embodiments, the terms "growth substrate", or "growth medium", which are used hereinthroughout interchangeably, are intended to mean a medium used for the growth of bacteria in a culture comprising components necessary for growth of the bacteria, such as, without limitation, a carbon/energy source.

Typically, the composition of the present invention may be produced by growing the disclosed strain in a liquid medium or on agar plates. The liquid medium may be any suitable nutrient medium comprising carbon and nitrogen sources and inorganic salts. Suitable media are available or may be available from commercial sources. Said media may be in liquid form a solid form.

In some embodiments, the growth substrate is a selective growth medium. In some embodiments, the selective growth medium is designed to suppress the growth of some microorganisms while allowing the growth of other(s) (e.g., the disclosed microorganism).

In some embodiments, the selective growth medium comprises a sugar and/or an amino acid, or a derivative thereof.

The term "amino acid" (or "amino acids", also referred to as "amino acid type(s)") is understood to include, without being limited thereto, the twenty naturally occurring amino acids, as known in the art. Furthermore, unless stated otherwise, the term "amino acid" may refer to both D- and L-amino acids. Non-conventional or modified amino acids (e.g., synthetic), are also conceivable in some embodiments of the invention.

In some embodiments, the selective growth medium comprises one or more amino acids selected from, but are not limited to, Proline nitroanilide, γ-L-glutamyl p-nitroanilide, phenylalanine, glycine, arginine, and any combination thereof.

The term sugar is meant to include any mono-, di-, or tri-saccharide and any of their reduced or oxidized forms that still possess hydroxyl groups. Non-limiting examples of saccharides include, for example, fructose, glucose, sucrose, rhamnose, galactose, lactose, arabinose, glucuronic acid, maltose, and raffinose.

An exemplary derivative of sugar is glycoside. Another exemplary derivative of sugar is a sugar alcohol. The term "glycoside" is generic and the presence of a particular sugar residue is indicated by the appropriate term, as glucoside, galactoside, fructoside, etc. The glycoside may be considered to be derived from a monosaccharide, a disaccharide, a trisaccharide or even an oligosaccharide containing up to e.g., 9 sugar units.

In some embodiments, the selective growth medium comprises one or more sugar or sugar derivative selected from, but are not limited to, arabinose, mannose, sucrose, melibiose, galactose, inositol, glucoside, and any combination thereof.

In some embodiments, the glucoside is selected from, without being limited thereto, p-Nitrophenyl-β-glucoside (p-n-p-β-Glc), p-n-p-α-glucoside, and p-n-p-α-β-glucoside. In exemplary embodiments, the growth medium comprises p-n-p-α-β-glucoside.

In some embodiments, the selective growth medium comprises one or more materials selected from, without being limited thereto, p-n-p-xyloside, esculine, and urea.

In some embodiments, the selective growth medium comprises nitrofuration, ciprofloxacin, cephalothin, meropenem, norfloxacin, nalidixic acid, colistinsulfate, imipenem, cefeprime, aztreonam and cefuroxime.

(iii) Carriers

The compositions of the invention may also include one or more carrier, preferably one or more agriculturally acceptable carrier. In one embodiment the carrier, such as an agriculturally acceptable carrier, can be solid or liquid. Carriers useful herein include any substance typically used to formulate agricultural composition.

In one embodiment the agriculturally acceptable carrier maybe selected from the group comprising fillers, solvents, excipients, surfactants, suspending agents, speaders/stickers (adhesives), antifoaming agents, dispersants, wetting agents, drift reducing agents, auxiliaries, adjuvants or a mixture thereof.

Compositions of the invention may be formulated as, for example, concentrates, solutions, sprays, aerosols, immersion baths, dips, emulsions, wettable powders, soluble powders, suspension concentrates, dusts, granules, water dispersible granules, microcapsules, pastes, gels and other formulation types by well-established procedures. These procedures include mixing and/or milling of the active ingredients with agriculturally acceptable carrier substances, such as fillers, solvents, excipients, surfactants, suspending agents, speaders/stickers (adhesives), antifoaming agents, dispersants, wetting agents, drift reducing agents, auxiliaries and adjuvants.

In one embodiment solid carriers include but are not limited to mineral earths such as silicic acids, silica gels, silicates, talc, kaolin, attapulgus clay, limestone, lime, chalk, bole, loess, clay, dolomite, diatomaceous earth, aluminas calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders and the like. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or coloring agents which, when solid, may also serve as a diluent.

In one embodiment the carrier may also be liquid, for example, water; alcohols, particularly butanol or glycol, as well as their ethers or esters, particularly methylglycol acetate; ketones, particularly acetone, cyclohexanone, m ethyl ethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulfoxide, or N-methylpyrrolidone; liquefied gases; or the like or a mixture thereof.

Spreaders/stickers promote the ability of the compositions of the invention to adhere to plant surfaces. Examples of surfactants, spreaders/stickers include but are not limited to a polysorbate and a nonionic surfactant that has a hydrophilic polyethylene oxide chain, alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose. Where selected for inclusion, one or more agricultural surfactants, such as Tween are desirably included in the composition according to known protocols.

Wetting agents reduce surface tension of water in the composition and thus increase the surface area over which a given amount of the composition may be applied. Examples of wetting agents include but are not limited to salts of polyacrylic acids, salts of lignosulfonic acids, salts of phenolsulfonic or naphthalenesulfonic acids, polycondensates of ethylene oxide with fatty alcohols or fatty acids or fatty esters or fatty amines, substituted phenols (particularly alkylphenols or arylphenols), salts of sulfosuccinic acid esters, taurine derivatives (particularly alkyltaurates), phosphoric esters of alcohols or of polycondensates of ethylene oxide with phenols, esters of fatty acids with polyols, or sulfate, sulfonate or phosphate functional derivatives of the above compounds.

As described above, the compositions of the present invention may be used alone or in combination with one or more other agricultural agents, including pesticides, insecticides, acaracides, additional fungicides, bactericides, herbicides, antibiotics, antimicrobials, nemacides, rodenticides, entomopathogens, pheromones, attractants, plant growth regulators, plant hormones, insect growth regulators, chemosterilants, microbial pest control agents, repellents, viruses, phagostimulents, plant nutrients, plant fertilisers and biological controls. When used in combination with other agricultural agents the administration of the two agents may be separate, simultaneous or sequential. Specific examples of these agricultural agents are known to those skilled in the art, and many are readily commercially available.

Examples of fungicides include but are not limited to the following classes of fungicides: carboxamides, benzimidazoles, triazoles, hydroxypyridines, dicarboxamides, phenylamides, thiadiazoles, carbamates, cyano-oximes, cinnamic acid derivatives, morpholines, imidazoles, beta-methoxy acrylates and pyridines/pyrimidines. Further examples of fungicides include but are not limited to natural fungicides, organic fungicides, sulphur-based fungicides, copper/calcium fungicides and elicitors of plant host defences. Examples of natural fungicides include but are not limited to whole milk, whey, fatty acids or esterified fatty acids. Examples of organic fungicides include but are not limited to any fungicide which passes an organic certification standard such as biocontrol agents, natural products, elicitors (some of may also be classed as natural products), and sulphur and copper fungicides (limited to restricted use). In some embodiments non-organic fungicides may be employed.

Examples of pesticides include but are not limited to azoxystrobin, bitertanol, carboxin, Cu2O, cymoxanil, cyproconazole, cyprodinil, dichlofluamid, difenoconazole, diniconazole, epoxiconazole, fenpiclonil, fludioxonil, fluquiconazole, flusilazole, flutriafol, furalaxyl, guazatin, hexaconazole, hymexazol, imazalil, imibenconazole, ipconazole, kresoxim-methyl, mancozeb, metalaxyl, R-metalaxyl, metconazole, oxadixyl, pefurazoate, penconazole, pencycuron, prochloraz, propiconazole, pyroquilone, SSF-109, spiroxamin, tebuconazole, thiabendazole, tolifluamid, triazoxide, triadimefon, triadimenol, triflumizole, triticonazole and uniconazole.

It is important that any additives used are present in amounts that do not interfere with the effectiveness of the biological control agents.

The composition can further comprise a stabilizer. As used herein, the term "stabilizer" refers to an excipient which maintains the chemical structure and/or biological activity of the bacterium of the present invention. In some embodiments, the stabilizer is selected from the group consisting of Tweens, tritons, tyloxapol, pluronics, Brijcs, Spans, poloxamers and cmulphors. In some embodiments, the stabilizer is polyvinylpyrrolidone (PVP). In some embodiments, the stabilizer is polysorbate. In some embodiments, the stabilizer is selected from the group consisting of polysorbate, sodium dodecyl benzene sulfate (SDBS), Poly(ethylene glycol)-block-poly(propylene glycol)-block-poly(ethylene glycol), and Polyethylene glycol sorbitan monolaurate (Tween 20).

The composition can further comprise a buffering agent. The "buffering agent" means an agent(s) which is added to the composition in order to adjust the pH value in a solution preparation or in a lyophilized preparation when reconstituted. Determination of this pH optimum can be achieved using methods generally available in the art. Representative buffering agents that can be included in the compositions of the present invention are, for example, phosphate buffer, acetate buffer, Tris buffer and citrate buffer. Each possibility is a separate embodiment of the invention. The buffering agent adjusts the pH value of the solution so that the stability of bacterium or the compounds therein is maintained. The pH value of the present composition is, in some embodiments, in the range of about 5 to about 8.

The compositions may be prepared in a number of forms. One preparation comprises a powdered form of a composition of the invention. In a further form, the composition is mixed with a diluent such as water to form a spray, foam, gel or dip and applied appropriately using known protocols.

Compositions formulated for other methods of application such as injection, rubbing or brushing, may also be used, as indeed may any known art method. Indirect applications of the composition to the plant surroundings or environment such as soil, water, or as seed coatings are also contemplated.

The concentration at which the compositions of the invention are to be applied so as to be effective biological control agents may vary depending on the end use, physiological condition of the plant; type (including bacterial species), concentration and degree of pathogen infection; temperature, season, humidity, stage in the growing season and the age of plant; number and type of conventional pesticides or other treatments (including fungicides) being applied; and plant treatments (such as leaf plucking and pruning).

Repeated applications at the same or different times in a crop cycle are contemplated. The compositions of the invention may be applied either earlier or later in the season. This may be over flowering or during fruiting, tuber emergence, and the like. The compositions of the invention may also be applied immediately prior to harvest, or after harvest.

The compositions set forth above can be formulated in any manner. Non-limiting formulation examples include but are not limited to dried grains such as Emulsifiable concentrates (EC), Wettable powders (WP), Soluble liquids (SL), Aerosols, Ultra-low volume concentrate solutions (ULV), Soluble powders (SP), Microencapsulation, Water dispersed granules (WDG), Flowables (FL), Microemulsions (ME), Nano-emulsions (NE), etc. In any formulation described herein, percent of the active ingredient is well within the skills of the artisan e.g., within a range of 0.01% to 99.99%.

The compositions may be in the form of a liquid, gel, solid, or biofumigant. A solid composition can be prepared by soaking a solid carrier in a solution of active ingredient(s) and drying the suspension under mild conditions, such as evaporation at room temperature or vacuum evaporation at 65° C. or lower. A solid composition can also be dried grains grown with the strain. The composition may additionally comprise a surfactant to be used for the purpose of emulsification, dispersion, wetting, spreading, integration, disintegration control, stabilization of active ingredients, and improvement of fluidity or rust inhibition.

Compounds Derived from *Dyella*-Like Bacterium and Analogs thereof.

According to some embodiment, the composition comprises a plurality of compounds (e.g., volatile organic compounds (VOC)s) being produced from a biologically pure culture of the disclosed bacterium. According to some embodiment, the composition comprises a plurality of synthetic compounds identical to, analogous to, or derived from, said compounds.

In some embodiments, said plurality of compounds are selected from Quinolinecarboxaldehyde, Hydroxymethyl-2-furaldehyde, or any derivative thereof.

In some embodiments, the composition comprises Quinolinecarboxaldehyde, or Hydroxymethyl-2-furaldehyde, or any derivative thereof. In some embodiments, the composition comprises Quinolinecarboxaldehyde, and Hydroxymethyl-2-furaldehyde, any derivative thereof.

In some embodiments, there is provided a composition comprising Quinolinecarboxaldehyde, and Hydroxymethyl-2-furaldehyde, or any derivative thereof. In some embodiments, the composition comprises Quinolinecarboxaldehyde, and Hydroxymethyl-2-furaldehyde, or any derivative thereof, in a ratio of 1:10 to 10:1. In some embodiments, the composition comprises Quinolinecarboxaldehyde, and Hydroxymethyl-2-furaldehyde, or any derivative thereof, in a ratio of 1:5 to 5:1. In some embodiments, the composition comprises Quinolinecarboxaldehyde, and Hydroxymethyl-2-furaldehyde, or any derivative thereof, in a ratio of 1:4 to 4:1. In some embodiments, the composition comprises Quinolinecarboxaldehyde, and Hydroxymethyl-2-furaldehyde, or any derivative thereof, in a ratio of 1:3 to 3:1. In some embodiments, the composition comprises Quinolinecarboxaldehyde, and Hydroxymethyl-2-furaldehyde, or any derivative thereof, in a ratio of 1:2 to 2:1. In some embodiments, the composition comprises Quinolinecarboxaldehyde, and Hydroxymethyl-2-furaldehyde, or any derivative thereof, in a ratio of 1:1.5 to 1.5:1. In some embodiments, the composition comprises Quinolinecarboxaldehyde, and Hydroxymethyl-2-furaldehyde, or any derivative thereof, in a ratio of 1:1.1 to 1.1:1.

In some embodiments, the Quinolinecarboxaldehyde or a derivative thereof has a structure represented by Formula I:

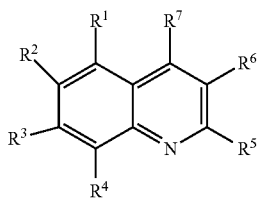

wherein each of $R_1$ to $R_5$ represents a substituent, and wherein one to four substituents from $R^1$ to $R^7$, in each instance, comprise or are selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, or is a fused ring, and at least one of $R^1$ to $R^5$ is independently in the form represented by Formula I2:

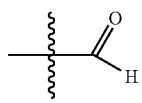 [SMILES: *C=O]

In some embodiments, the Quinolinecarboxaldehyde has the structure of Formula II (also referred to as 4-Quinolinecarboxaldehyde):

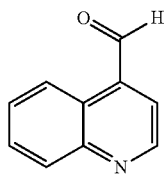

In some embodiments a derivative of 5-(Hydroxymethyl)-2-furfural is selected from, but is not limited to: 5-Methylfurfural, 2-Furyl alkyl ketone, 2,5-Furandicarboxaldehyde, Furfural, Furfuryl alcohol, 5-alkyl-furfural, 2,5-Furandicarboxylic acid. Herein, "alkyl" may refer to C1-C5 alkyl, e.g., methyl.

As demonstrated in the Examples section that follows, the present inventors have shown that the combination of Quinolinecarboxaldehyde, and Hydroxymethyl-2-furaldehyde exhibits a synergistic antimicrobial effect.

In some embodiments, the term synergism, or any grammatical derivative thereof, is defined as the simultaneous action of two or more compounds in which the total response of an organism to the combination is greater than the sum of the individual components. Although many combinations of antimicrobial compounds have been studied, a synergistic effect is rarely revealed and the global use of antimicrobial combinations with synergistically enhanced activity is rather limited.

Extraction Methods

In some embodiments, the compounds described herein are extracted from a medium or a supernatant comprising the disclosed bacteria.

As used herein, the term "extract", or any grammatical derivative thereof, includes but is not limited to products (e.g., concretes, oleoresins, distillates, dry powder extracts, fluid extracts and residues) obtained from a source such as a plant or animal through an extraction process such as distillation, organic extraction, alcoholic extraction, aqueous extraction and solvent extraction.

Non-limiting examples solvents used for extraction include methanol, acetone, tert-butyl ether (MTBE), chloroform and hexan. In exemplary embodiments, the solvents are selected from methanol and acetone.

Fractional distillation and/or absorption chromatography are also non-limiting examples of methods to extract the desired product produced by the bacterial isolates of the present invention. Fractional distillation is known in the art as the separation of a mixture into its component parts, or fractions, such as in separating chemical compounds by their boiling point by heating them to a temperature at which several fractions of the compound will evaporate. Absorption chromatography is a physical separation method in which the components of a mixture are separated by differences in their distribution between two phases, one of which is stationary (stationary phase) while the other (the mobile phase) moves through it in a definite direction. The substances must interact with the stationary phase to be retained and separated by it.

Gas chromatography is a well-known technique for fractionating and determining the relative amounts of various components in a sample containing a mixture of compounds of differing volatilities. For example, the sample is vaporized and the entire resulting quantity of gases is passed through an analytical chromatography column. Chromatographic processes such as gas chromatography can rapidly determine the volatiles content of a multicomponent sample, such as would be produced by the fungal isolates of the present invention.

Antibacterial Activity

In some embodiments, the invention provides an antibacterial composition. In some embodiments, the invention provides an anti-phytopathogenic composition.

In some embodiments, the compounds of the invention and compositions comprising same, are characterized by having anti-bacterial activity, e.g., lytic activity against a target bacterium.

In some embodiments, there is provided a method of treating or preventing plant infection, for example phytoplasma plant infection. In some embodiments, the method comprises the step of treating the plant with one of the disclosed composition thereby reducing the symptoms or preventing the phytoplasma plant infection.

Thus, according to an aspect of the invention there is provided a method of killing a phytopathogen or reducing symptoms thereof, the method comprising exposing the phytopathogen to an effective amount of a composition comprising a biologically pure culture of the disclosed bacterium or at least one compound being produced by the biologically culture and capable of killing the phytopathogen or reducing damage or symptoms thereof.

According to an additional or an alternative aspect of the invention there is provided a method for reducing overall damage to a plant or plant part caused by a phytopathogen, the method comprising exposing the plant or plant part to an effective amount of any of the disclosed composition (e.g., the bacterium composition in any embodiment thereof) or at least one compound being produced by the biologically culture and capable of killing the phytopathogen or reducing symptoms thereof, thereby reducing overall damage to the plant or plant part.

The phrases "anti-phytopathogenic activity" and "anti-phytopathogenic efficacy" are used interchangeably herein and refer to the ability of certain agents, such as certain microorganisms, to antagonise one or more phytopathogens. The term "anti-bacterial" means an ability to antagonise one or more bacteria, particularly one or more phytopathogenic bacteria. According an anti-bacterial agent, such as an anti-fungal bacterial strain, is an agent that is an antagonist of one or more fungi, preferably of one or more phytopathogenic fungi. Such an agent is herein considered to have anti-fungal efficacy.

The term "biological control agent" (BCA) as used herein refers to a biological agent which acts as an antagonist of one or more pathogens, such as a phytopathogenic insects, a phytopathogenic bacteria, or a phytopathogenic protozoa, or is able to control one or more phytopathogens. Antagonism may take a number of forms. In one form, the biological control agent may simply act as a repellent. In another form, the biological control agent may render the environment unfavourable for the phytopathogen. In a further, preferred form, the biological control agent may parasitise, incapacitate, render infertile, impeded the growth of, and/or kill the phytopathogen. The antagonistic mechanisms include but are not limited to antibiosis, parasitism, infertility, and toxicity. Therefore, agents which act as antagonists of one or more phytopathogens can be said to have anti-phytopathogenic efficacy. For example, an agent that is an antagonist of a phytopathogenic insects can be said to have mycopathogenic efficacy.

As used herein, a "biological control composition" is a composition comprising or including at least one biological control agent that is an antagonist of one or more pathogens (e.g., phytopathogens). Such control agents include, but are not limited to, agents that act as repellents, agents that render the environment unfavourable for the pathogen, and agents that incapacitate, render infertile, and/or kill the pathogen. Accordingly, such a composition is herein considered to have anti-phytopathogenic efficacy.

Accordingly, as used herein an "anti-phytopathogenic composition" is a composition which comprises or includes at least one agent that is an antagonist of one or more phytopathogens. Such a composition is herein considered to have anti-phytopathogenic efficacy.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "control" or "controlling" as used herein generally comprehends preventing, reducing, or eradicating pathogen infection or inhibiting the rate and extent of such infection, or reducing the pathogen population in or on a plant or its surroundings, wherein such prevention or reduction in the infection(s) or population(s) is statistically significant with respect to untreated infection(s) or populatiori(s). Curative treatment is also contemplated. Preferably, such control is achieved by increased mortality amongst the pathogen population.

As used herein the term "reducing" refers to at least 20%, 30%, 40%, 50%, 60%, 70%, 80% 90% or more, reduction of growth or even 100% arrest of growth in a given time as compared to the growth in that given time of the pathogen not being exposed to the treatment as described herein.

As used herein, the term "preventing" in the context of antimicrobial, indicates that the growth rate of the microorganism cells is essentially nullified or is reduced by at least 20%, at least 30%, at least 40%, at least 50%, at least 60%, at least 70%, at least 80%, at least 90%, including any value therebetween, of the appearance of the microorganism in a comparable situation lacking the presence of the disclosed bacteria. Alternatively, preventing means a reduction to at least 15%, 10% or 5% of the appearance of the microorganism cells in a comparable situation lacking the presence of the disclosed or a composition containing same. Methods for determining a level of appearance of a microorganism cells are known in the art.

The effect of the compositions of the invention may also be described as pesticidal or pestistatic.

As used herein, the term "endophyte" refers to an organism capable of living within a plant or is otherwise associated therewith, and does not cause disease or harm the plant otherwise (i.e. is capable of living symbiotically with the plant). Endophytes can occupy the intracellular or extracellular spaces of plant tissues, including the leaves, stems, flowers, fruits, seeds, or roots. An endophyte can be for example a bacterial or fungal microorganism.

The term "plant" as used herein encompasses not only whole plants, but extends to plant parts, cuttings as well as plant products including roots, leaves, flowers, seeds, stems, callus tissue, nuts and fruit, bulbs, tubers, corms, grains, cuttings, root stock, or scions, and includes any plant material whether pre-planting, during growth, and at or post-harvest. Plants that may benefit from the application of the present invention cover a broad range of agricultural and horticultural crops.

As used herein, the term "phytopathogen" refers to an organism that is pathogenic to plants. The phytopathogenic organism typically refers to a unicellular organism e.g., including bacteria, as well as fungi, oomycetes, chytrids, algae, and nematodes. The pathogen may be in any developmental stage.

According to a specific embodiment, the phytopathogen is a microorganism (e.g., bacterium). Phytopathogenic bacteria typically include, but are not limited to the genera, *Agrobacterium* (e.g., *A. tumefaciens*); *Erwinia, Pantoea, Pectobacterium, Serratia, Acidovorax, Pseudomonas, Ralstonia, Rhizobacter, Rhizomonas, Xanthomonas, Xylophilus, Rhizobium, Bacillus, Clostridium, Arthrobacter, Clavibacter, Curtobacterium, Leifsonia, Rhodococcus, Streptomyces*, and *Xanthomonas* (*X. axonopodis, X. oryzae* pv. oryzae, *X. vesicatoria*).

In a particular embodiment, phytopathogenic bacterium is selected from the group consisting of *Clavibacter, Xanthomonas, Pseudomonas* (e.g., *P. syringae*), and *Pectobacterium* (e.g., *P. carotovorum*).

In some embodiments, the pathogens are pathogens typically residing in plant vascular systems (e.g., xylem or phloem). In some embodiments, the pathogens are selected from phloem-restricted pathogens. In some embodiments, phloem-restricted pathogens are selected from spiroplasmas, and phytoplasmas, mycoplasma and *libaribacters*. In exemplary embodiments, the phloem-restricted pathogen is selected from *Spiroplasma melliferum* and *Phytoplasma solani*.

Phytoplasmas can be detected using means known in the art including electron microscopy and molecular techniques including DNA probes, polymerase chain reaction (PCR), and enzyme linked immuno-absorbent assay (ELISA).

In one embodiment, the bacterial cell(s) are stored such that it is effective for killing the phytopathogen or reducing growth thereof. For example, the cells may be dried (e.g. freeze-dried) or frozen. In another embodiment, the cells are in a culture. Media for propagating the cells may be selected from the group consisting of: soil, hydroponic apparatus, and/or artificial growth medium.

Compositions may comprise whole broth cultures, liquid or solid cultures, or suspensions of the disclosed bacterial cells, having at least one of the identifying characteristics of the disclosed strains, as well as supernatant, filtrate and/or extract or one or more and more particularly a plurality of (i) metabolites, (ii) isolated compounds (iii) volatiles derived from the bacteria disclosed herein, or (iv) synthetic compounds (e.g., comprises Quinolinecarboxaldehyde, or Hydroxymethyl-2-furaldehyde) or derivatives of same having the activity of killing the phytopathogen or reducing the growth thereof.

The composition may be combined or used with another microorganism and/or pesticide (e.g., nematicide, bactericide, fungicide, insecticide). In some embodiments, the bacterium composition further comprises a material selected from a fertilizer, a pesticide, or any combination thereof.

The term "fertilizer" as used herein, refers to any substance which, when applied to a substrate, e.g., soil, leaves, hydroponic solution etc., enriches or fertilizes that substrate by providing nutrients for the organism's, e.g., plant's, necessary biological functions, e.g., growth, flowering etc.

According to further characteristics in some embodiments of the invention described below, the pesticide is selected from the group consisting of acaricides, miticides, algicides, antifeedants, avicides, bactericides, bird repellants, chemosterilants, fungicides, herbicide safeners, herbicides, insect attractants, insect repellants, insecticides, mammal repellants, mating disrupters, molluscicides, nematicides, plant activators, plant growth regulators, rodenticides, synergists, and virucides, and any combination thereof.

According to further characteristics in some embodiments of the invention described below, the herbicide is selected from the group consisting of chlorotriazine herbicides, chloroacetanilide herbicides, and halogenated aliphatic herbicides.

Furthermore, the pesticide may be a single site anti-fungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine), a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole), myclobutanil, and a quinone outside inhibitor (e.g., strobilurin). The strobilurin may include but is not limited to azoxystrobin, kresoxim-methoyl or trifloxystrobin. In yet another particular embodiment, the anti-fungal agent is a quinone, e.g., quinoxyfen (5,7-dichloro-4-quinolyl 4-fluorophenyl ether). The anti-fungal agent may also be derived from a Reynoutria extract.

The fungicide can also be a multi-site non-inorganic, chemical fungicide selected from the group consisting of chloronitrile, quinoxaline, sulphamide, phosphonate, phosphite, dithiocarbamate, chloralkylhios, phenylpyridinamine, and cyano-acetamide oxime As noted above, the composition may further comprise a nematicide. This nematicide may include but is not limited to chemicals such as organophosphates, carbamates, and fumigants, and microbial products such as avermectin, *Myrothecium* spp., Biome (*Bacillus firmus*), *Pasteuria* spp., *Paecilomyces* spp., and organic products such as saponins and plant oils.

In the case that the composition is applied to a seed, it can be done as one or more coats prior to planting the seed using one or more seed coating agents including, but are not limited to, ethylene glycol, polyethylene glycol, chitosan, carboxymethyl chitosan, peat moss, resins and waxes or chemical fungicides or bactericides with either single site, multisite or unknown mode of action using methods known in the art.

As noted above, the compositions set forth above may be applied using methods known in the art. Specifically, these compositions may be applied to and around plants or plant parts. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include, but are not limited to, harvested material, and vegetative and generative propagation material, for example cuttings, tubers, rhizomes, offshoots and seeds In some embodiments, the plants are vascular plants. Vascular plant comprises vascular tissue e.g., phloem. Phloem is the plant tissue that translocates the products of photosynthesis from mature leaves to areas of growth and storage.

In some embodiments, grapevines are amendable for treatment using the compositions of the invention. Exemplary vines are selected from, without being limited thereto, Chardonnay, Cabernet Sauvignon, Pinot noir, Riesling, Sauvignon blanc, and Sémillon, Sangiovese and Garganega.

In exemplary embodiments, the plant is grapevine. In another exemplary embodiment, the plant is periwinkle. In another exemplary embodiment, the plant is a carrot.

As mentioned, the plant, part thereof or the phytopathogens are exposed to an effective amount of the composition. Exposure as used herein means that a sufficient amount of the compounds of the invention effect the killing of the phytopathogen or reduce growth thereof.

Exposing the plant, part thereof or the phytopathogen to the compositions set forth above may be carried out directly or by allowing the disclosed compositions to act on their surroundings, habitat or storage space by, for example, immersion, coating, dipping, spraying, evaporation, fogging, scattering, painting on, or injecting.

The compositions may also be applied to the soil using methods known in the art. These include but are not limited to (a) drip irrigation or chemigation; (b) soil incorporation; (c) seed treatment.

The compositions, be used as pesticides and in particular, may be used as insecticides, nematicides, fungicides and bactericides, alone or in combination with one or more pesticidal substances set forth above and applied to plants, plant parts, substrate for growing plants or seeds.

The compositions may be combined with other enhancing compounds for the compositions such as, but not limited to, amino acids, chitosan, chitin, starch, hormones, minerals, synergistic microbes to increase efficacy and promote benefits to plants.

Seed Coatings

According to some embodiments of the present invention there is provided a composition comprising a plant seed and a capsule encapsulating the plant seed, wherein the capsule comprises (a) the bacterium of the invention, and (b) a biocompatible material.

In some embodiments, the term "biocompatible" is defined as the ability of a material to perform with an appropriate host response in a specific application.

In the context of biomaterial applications, biocompatibility refers to the ability to perform as a supportive matrix to an appropriate activity, without eliciting any undesirable effects, or inducing any undesirable local or systemic responses in the host.

In the context of embodiments of the present invention, a "biocompatible material" describes a material (e.g., a natural or synthetic polymer) or matrix (e.g., hydrogel or scaffold) that does not interfere, and preferably provides a suitable environment for biological activity.

In some embodiments, the capsule is in the form of a core-shell. In some embodiments, the core is or comprises one or more seeds. In some embodiments, the shell is or comprises a biocompatible material and the bacterium of the invention.

The term "core-shell structure" generally refers to a solid material, wherein the solid material is a particulate material, and wherein individual particle(s) is characterized by containing at least two different types of materials which may be distinguished from one another by their composition and/or by their structure and/or by their placement within the particle, wherein one or more materials of a certain type are contained in the interior portion of the composite.

The outer portion of the capsule comprising the surface is designated by the terms "shell" or "coating layer".

In some embodiments, the core-shell structure is a closed structure. The term "closed" as used herein, is a relative term with respect to the size, the shape and the particle or composition of two entities, namely an entity that defines an enclosure (the enclosing entity) and the entity that is being at least partially enclosed therein. In general, the term "closed" refers to a morphological state of an object which has discrete inner (e.g., the seed) and outer surfaces which are substantially disconnected, wherein the inner surface constitutes the boundary of the enclosed area.

In some embodiments, the seeds may be coated using any process known in the art. For example, the seeds may be coated in binder and then tumbled in the polymeric powder. In some embodiments, the seed is tumbled in a polymeric powder without binder, to cause a dusting of the powder to adhere to the seeds.

Additional components may be included in the coating. Such components may be any one or more of the following, in any combination:

a component having the effect of chemically and/or mechanically stabilizing and/or preserving the seeds: for example to increase their storage life, reduce their susceptibility to environmental contaminants or to reduce the likelihood of them being broken up during drilling/sowing;

a component having the effect of enhancing the fertilizing effect of the coating: for example by accelerating or retarding the breakdown of the coating in the field;

a component having the effect of protecting or enhancing the growth of crops by means other than fertilizing: for example a herbicide, fungicide, insecticide, rodenticide, hormone, plant stimulant or mycorrhizal fungus or spore;

a fertilizer composition: for example a source of nitrogen and/or phosphorus and/or any other biologically active ingredient such as boron, cobalt to promote growth of the plant seed or partner organisms;

a pigment;

a binder;

a component having the effect of altering soil pH: for example lime, sulfur or a sulfate; and an inert porous matrix might be added to permit improved water, air or nutrient passage to the seed.

Such a component may be added at various stages in the process, for example it may be combined with the coating powder before or after the formation of a slurry as described above, or with the binder prior to the mixing stage as described above, or it may be sprayed or otherwise coated on to the seeds before or after drying. The component may be sprayed or otherwise coated on to the seed before the seed is coated with the slurry, for example one or more components may be applied to the seed prior to the seeds being coated by the slurry.

In some embodiments, the exterior coatings of seed is formed of one or more layers and one or more of the additional components described above may be present in at least one of those layers. In practice, the mean thickness of the coating could be in the range from 0.1 to 1.0 mm, the mean thickness of the coating may also be in the range from 0.1 to 2.0 mm, but the range can be chosen to suit the seed in question and the desired mass of coating per seed.

In some embodiments, the coating, is for example above e.g., 0.5%, 1%, 5%, 10%, 20%, 50%, 60%, 70%, 80%, 90%, or above 95% by weight.

The mass of coating with which each seed is coated can be controlled through the choice of binder, or the relative proportions of binder and coating material.

In some embodiments, the biocompatible material comprises an adhesive material.

In some embodiments, the adhesive material is selected from, but is not limited to, guar, derivatized guar, polyacrylamide, poly(methacrylic acid), poly(acrylic acid), polyacrylate, poly(ethylene glycol), phosphonate-end capped polymers, polyethyleneoxide, poly(vinyl alcohol), polyglycerol, polytetrahydrofuran, polyamide, starch, derivatized starch, waxy maize, sorghum, waxy sarghum, sago, dextrin, chitin, chitosan, alginate compositions, gum, pectin, cellulose, or any combination or derivative thereof.

In some embodiments, the biocompatible material comprises a mineral.

In some embodiments, the term "mineral" refers to one or more evaporate minerals is/are adhered to the exterior of the seed. The coating may comprise a matrix of binder in which particles of the one or more evaporate minerals are embedded. The coating may fully or partially enclose the seed.

In some embodiments, the binder may be susceptible to degradation on exposure to moisture. The binder may be such as to release at least 50% of the mineral particles In some embodiments, the binder is selected from, but is not limited to, gelatin, polyvinyl acetate, polyvinylpyrolidones, dextrin, malto-dextrins, polysaccharides, fats, oils, proteins, shellacs, vinylidene chloride, vinylidene chloride copolymers, calcium lignosulfonates, acrylic copolymer, polyvinylacrylate, zein, chitosan, polyethylene oxide, acrylimide polymer, polyhydroxyethyl acrylate, a methylacrylimide monomer, alginate, polychloroprene, syrup, or any combination thereof.

Chemical Definitions

As used herein, the term "alkyl" describes an aliphatic hydrocarbon including straight chain and branched chain groups. Preferably, the alkyl group has 21 to 100 carbon atoms, and more preferably 21-50 carbon atoms. Whenever a numerical range; e.g., "21-100", is stated herein, it implies that the group, in this case the alkyl group, may contain 21 carbon atom, 22 carbon atoms, 23 carbon atoms, etc., up to and including 100 carbon atoms. In the context of the present invention, a "long alkyl" is an alkyl having at least 20 carbon atoms in its main chain (the longest path of continuous covalently attached atoms). A short alkyl therefore has 20 or less main-chain carbons. The alkyl can be substituted or unsubstituted, as defined herein.

The term "alkyl", as used herein, also encompasses saturated or unsaturated hydrocarbon, hence this term further encompasses alkenyl and alkynyl. The term "alkenyl" describes an unsaturated alkyl, as defined herein, having at least two carbon atoms and at least one carbon-carbon double bond. The alkenyl may be substituted or unsubstituted by one or more substituents, as described hereinabove. The term "alkynyl", as defined herein, is an unsaturated alkyl having at least two carbon atoms and at least one carbon-carbon triple bond. The alkynyl may be substituted or unsubstituted by one or more substituents, as described hereinabove. The term "cycloalkyl" describes an all-carbon monocyclic or fused ring (i.e. rings which share an adjacent pair of carbon atoms) group where one or more of the rings does not have a completely conjugated pi-electron system. The cycloalkyl group may be substituted or unsubstituted, as indicated herein.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted, as indicated herein. The term "alkoxy" describes both an —O-alkyl and an —O-cycloalkyl group, as defined herein. The term "aryloxy" describes an —O-aryl, as defined herein. Each of the alkyl, cycloalkyl and aryl groups in the general formulas herein may be substituted by one or more substituents, whereby each substituent group can independently be, for example, halide, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule. Additional substituents are also contemplated.

The term "halide", "halogen" or "halo" describes fluorine, chlorine, bromine or iodine. The term "haloalkyl" describes an alkyl group as defined herein, further substituted by one or more halide(s). The term "haloalkoxy" describes an alkoxy group as defined herein, further substituted by one or more halide(s).

The term "hydroxyl" or "hydroxy" describes a —OH group. The term "thiohydroxy" or "thiol" describes a —SH group. The term "thioalkoxy" describes both an —S-alkyl group, and a —S-cycloalkyl group, as defined herein. The term "thioaryloxy" describes both an —S-aryl and a —S-heteroaryl group, as defined herein.

The term "amine" describes a —NR'R" group, with R' and R" as described herein.

The term "heteroalicyclic" or "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofurane, tetrahydropyrane, morpholino and the like.

The term "carboxy" or "carboxylate" describes a —C(=O)—OR' group, where R' is hydrogen, alkyl, cycloalkyl, alkenyl, aryl, heteroaryl (bonded through a ring carbon) or heteroalicyclic (bonded through a ring carbon) as defined herein.

The term "carbonyl" describes a —C(=O)—R' group, where R' is as defined hereinabove.

The above-terms also encompass thio-derivatives thereof (thiocarboxy and thiocarbonyl). The term "thiocarbonyl" describes a —C(=S)—R' group, where R' is as defined hereinabove. A "thiocarboxy" group describes a —C(=S)—OR' group, where R' is as defined herein.

A "sulfinyl" group describes an —S(=O)—R' group, where R' is as defined herein. A "sulfonyl" or "sulfonate" group describes an —S(=O)$_2$—R' group, where Rx is as defined herein.

A "carbamyl" or "carbamate" group describes an —OC(=O)—NR'R" group, where R' is as defined herein and R" is as defined for R'. A "nitro" group refers to a —NO$_2$ group. A "cyano" or "nitrile" group refers to a —C≡N group. As used herein, the term "azide" refers to a —N$_3$ group. The term "sulfonamide" refers to a —S(=O)$_2$—NR'R" group, with R' and R" as defined herein.

The term "phosphonyl" or "phosphonate" describes an —O—P(=O)(OR')$_2$ group, with R' as defined hereinabove. The term "phosphinyl" describes a —PR'R" group, with R' and R" as defined hereinabove.

The term "alkaryl" describes an alkyl, as defined herein, which substituted by an aryl, as described herein. An exemplary alkaryl is benzyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

As used herein, the terms "halo" and "halide", which are referred to herein interchangeably, describe an atom of a halogen, that is fluorine, chlorine, bromine or iodine, also referred to herein as fluoride, chloride, bromide and iodide.

The term "haloalkyl" describes an alkyl group as defined above, further substituted by one or more halide(s).

As used herein the term "about" refers to ±10%.

The terms "comprises", "comprising", "includes", "including", "having" and their conjugates mean "including but not limited to." The term "consisting of" means "including and limited to." The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Insects and Plants:

Ten planthoppers *Hyalesthes obsoletus* (Cixiidae), a vector of grapevine phytoplasma, were collected in the Golan Heights, Israel on October 2011 and were either placed directly in 97% ethanol or used alive for microorganism's isolation.

Grapevines *Vitis vinifera* from the variety 'Chardonnay' and periwinkle (*Vinca* spp.) plantlets were established by cuttings 2-3 cm of stem with bud and planting it in 30 ml glass tube containing growth media (sucrose 30 g/L, thiamine 0.4 mg/1, VPM 2.35 g/L (Duchefa), activated charcoal 2.5 g/L and myoinositole 100 mg/L). The plantlets were grown in controlled conditions under 24° C., 16:8 L:D regime. Plantlets from both genera were 6-8 weeks old at the time the experiments started.

Bacteria Isolation and Identification:

To identify potential culturable bacteria from *H. obsoletus*, 10 individual insects were surface sterilized, by submerging the insects in ampicillin and tetracycline mixture for 5 min followed by three sets of washings with sterile saline solution (2 min each). The samples were then placed in an Eppendorf tube containing 300 μL sterile saline solution (9% NaCl), ground using pestle and diluted in through a 10 fold series. Aliquots of 150 μL of dilution $10^2$-$10^7$ were then spread on crystal violet (CV) agar (66 g/L sucrose, 10 g/L sorbitol, 2 g/L Luria broth, 0.1% crystal violet and 15 g/L agar). Plates were kept at 28° C. in the dark, and colonies grown were identified by DNA sequence of the 16S rRNA gene and the internal transcribed spacer (ITS) domain amplified by PCR (Table 1).

Bacteria Growth:

Only one bacterium was isolated following the procedure described above. While it is closely related to the genus *Dyella*, it is most probably an un-described genus. In order to produce large quantities of bacterial inoculum, the bacteria were grown by transferring two loops from the CV plates culture to 250 mL liquid medium (6 g/L Luria broth, 2 g/L $K_2HPO_4$ and 0.5 g/L $KH_2PO_4$ pH 7) in 500 mL Erlenmeyer flask and incubating them at 28° C. at 150 rpm for 48 h. The bacteria were collected by centrifuge (3500 g; 15 min) and washed twice with phosphate saline buffer (PBS) (8 g/L NaCl, 0.2 KCl, 1.44 $Na_2HPO_4$ and 0.24 g/L $KH_2PO_4$ pH 7.5). Using a spectrophotometer (600 nm), the bacteria concentration was adjusted to OD=0.6 (~$10^6$ CFU/mL) with PBS. The concentration was confirmed by CFU counting on CV plate.

Bacterial Phylogenetic Analysis:

To further resolve the phylogenetic placement of the isolated bacteria, the nearly full 16S ribosomal RNA gene of this bacterium was amplified by the 27F+1513R primer set known to amplify most known Bacteria. The obtained product was sequenced and aligned with other Gamma and Beta proteobacteria which were retrieved from the SILVA ribosomal RNA gene database using MAFFT. The most appropriate nucleotide substitution model was determined using jModelTest 2 under the Bayesian information criterion, and was found to be TIM3+I+G. The maximum-likelihood phylogram was constructed using PhyML v3.1 implemented by SeaView v4.5.4. Bootstrapping support values were calculated from 1000 samples.

Bacteria genome analysis: Genomic DNA of the bacteria was isolated using the QIAamp DNA minikit according to the manufacturer's protocol. The quality of DNA was examined using the NanoDrop spectrophotometer. The genome sequencing was performed at the DNA Services Facility (Chicago, Ill.); a mate-pair library using the Nextera mate pair sample preparation kit was generated followed by genome sequencing in Illumina MiSeq, using 2.times.100 reads. De novo assembly was done by the software package CLC Genomics Workbench (v7.0), after quality trimming of raw sequence data (Q20), which yielded 6,709,847 reads from 333 contigs with approximately 86.7% fold coverage. The N50 quality measurement of the contigs was 42.2 kb, with an average contig size of 12.5 kb, and the largest contig assembled was approximately 191.2 kb. Gene prediction analysis and functional annotations were performed within the Integrated Microbial Genomes Expert Review (IMG ER) platform developed by the JGI, using the DOE-JGI Microbial Genome Annotation Pipeline. 3832 genes were predicted including 3757 CDS predictions using Prodigal V2.50, 49 tRNA genes using tRNAscan-SE 1.3.1 and 5 rRNA genes using HMMER 3.0. The predicted coding sequences were translated and used to search the TIGRFam, Pfam, KEGG, COG, and InterPro databases. 1945 protein-coding genes were assigned to 1381 KO categories.

Effective Metabolic overlap between phytoplasma was calculated using the NetCmpt tool. The software takes as an input the EC content of bacterial species, translates enzymatic content into species-specific topological networks, apply topology-based algorithm for the prediction of species-specific metabolic resources (NetSeed), and simulate growth following the exclusion of common resources. EC annotations for the bacteria's genome were retrieved from the Integrated Microbial Genomes Expert Review (IMG ER) platform developed by the JGI, using the DOE-JGI Microbial Genome Annotation Pipeline. EC annotations for the phytoplasma genome were retrieved from the KEGG database Antibiotics and secondary metabolites were predicted using the anti SMASH tool.

Antagonistic Test of the Bacteria's Supernatant:

To examine the ability of compounds excreted by the bacteria to inhibit *Spiroplasma melliferum* (a model bacterium which simulates phytoplasma infection), the bacteria was grown in a modified spiroplasma broth for 10 days. *Spiroplasma* cells were added to the supernatant and incubated at 29° C. for five days and then 1 µl of the incubated filtrate was inoculated to a fresh spiroplasma medium containing phenol red as a color marker for cells growth. The time required for color change is correlated with the initial spiroplasma concentration and was therefore used as a quantitative parameter for the inhibitory effect of the filtrates. *Spiroplasma* growing in fresh broth served as a positive control and the inhibitory effect of 0.5 µg/ml oxy-tetracycline was used as a reference. Inhibition index was defined as the ratio between the number of days to color change in the filtrate and the time required in the positive control. The inhibition index of 0.5 µg/ml oxytetracycline was 2.3. Thus, an isolate was considered inhibitory if the inhibition index of its filtrate was <2.

Identification of Active Fraction Extracts:

To identify volatiles with potential activity, the bacteria was grown in ca. 500 ml of medium containing 6 g/L LB, 2 g/L $K_2HPO_4$ and 0.5 g/L $KH_2PO_4$ for three days. The culture was centrifuged at 8000 rpm for 5 min, and the supernatant was extracted twice with 500 ml methyl tert-butyl ether (MTBE). The organic phase was evaporated to dryness using a gentle stream of nitrogen, and the dry extract was re-suspended with MTBE. This crude extract was separated to fractions by a column containing glass wool, sand and silica using different solvents: methanol, acetone, MTBE, chloroform, and hexan. The same extraction procedure was performed on sterile medium as a control. Each fraction, obtained by column separation, was evaporated to dryness using a gentle stream of nitrogen and the dried substances were re-suspended with 1 ml of ethanol. To examine the effect of each fraction extract on spiroplasma growth, the following test was preformed: 1 ml of spiroplasma medium, 10 µl spiroplasma cells and 20 µl of each fraction extract were incubated for three days at 29° C. *Spiroplasma* growing in fresh broth served as a positive control and sterile medium containing 20 µl of the phase extract was used as a negative control. Changes in the color from red to yellow indicated spiroplasma growth.

Volatiles Identification in the Bacteria's Active Fraction Extracts:

To identify the compounds in the chosen active fraction extracts (see results), 1 µl aliquot of the sample was injected into a GC-MSD apparatus (6890N/5973N Agilent Technologies Calif., USA) equipped with an Rxi-5 SIL MS (30 m*0.25 mm*0.25 µm) fused-silica capillary Column (Restek). Helium (Constant pressure 15.2 psi) was used as a carrier gas. The injector temperature was 250° C., set for splitless injection. The oven was set to 50° C. for 1 min, and then the temperature was increased to 260° C. at a rate of 5° C./min. The detector temperature was 280° C. The mass range was recorded from 41 to 350 m/z, with electron energy of 70 eV. A mixture of straight-chain alkanes (C7-C23) was injected into the column under the above-mentioned conditions for determination of retention indices. The GC-MS spectrum profiles were analyzed using the chamstation software the identification of the volatiles was assigned by comparison of their retention indices with those of literature and by comparison of spectral data with standard or with the W9N08 and HPCH2205 GC-MS libraries.

Antagonistic Test of the Bacteria's Specific Compounds:

After potential inhibitory compounds (4-Quinolinecarboxaldehyde and 5-Hydroxymethyl-2-furaldehyde) were identified in the active fraction extracts of the bacteria's supernatant, parallel synthetic compound were purchased (Sigma) and examined on spiroplasma in vitro: 1 ml of spiroplasma medium, 10 μl spiroplasma cells and 10 μl of each compound (final concentration of 1 milimolar) were incubated for three days at 29° C. *Spiroplasma* growing in fresh broth served as a positive control and sterile medium containing 20 μl of the phase extract was used as a negative control. Changes in the indicator color from red to yellow indicated spiroplasma growth.

Introduction of the Bacterium to the Plant:

The isolate's ability to penetrate grapevine was tested on 6-8 week old ex-vitro periwinkle and grapevine plantlets cv. Chardonnay. The plantlets were treated either in the isolate culture or in PBS (as control). All treatments were done in 3-5 replicates. Several methods were tested: A) ex-flasked plantlets were thoroughly washed, cut at root edge and submerged for 24 h pre-planting. B) stem injection: 20 μl of solution was injected to the base of the stem using 30 gauge needle. C) the leaves were pricked and smeared with solution using a cotton ear swab. The treated plantlets were than planted in commercial potting soil (EN12580, Tuf Merom Golan) in 0/5 L pots.

The presence of the isolate in the plants was examined by specific PCR (see, Table 1) from the leaves above inoculation point 7-10d post inoculation. 300 mg leaves were taken from each plant to test for the presence of the bacterium. Care was taken to sample new leaves that developed after the inoculation, to ensure no external contamination. The experiment was conducted in three replicates and PBS was used as a control.

Bacteria Detection:

PCR.

In order to determine the presence of both the bacteria and phytoplasma in their eukaryotic hosts, DNA was extracted from plants and insects; DNA from the new emerging leaves was extracted by CTAB method while DNA from each individual planthopper was extracted by grounding the insect in lysis buffer followed by incubation at 65° C. for 15 min and then 95° C. for 10 min. All DNA samples were kept at −20° C. until further use.

PCR reaction (25 μl) contained 10 μl of Apex™ Taq DNA Polymerase Master Mix (Genorama, Tartu, Estonia), 5 pmole of each primer, 12.5 μl DDW and 1 μl DNA template. The PCR consisted 35 cycle of 94° C. −0.5 min, annealing Tm-0.5 min (Table 1) and 72° C.-0.5 min followed by 10 min of 72° C. The bacteria was identified by two sets of primers aiming for the 16S rRNA gene and the ITS domain (Table 1) while phytoplasma presence was tested with nested PCR as previously described.

Microscope.

The bacteria culture was visualized under light microscope (BX61, Olympus). Fluorescence in situ hybridization (FISH) procedure was applied in order to verify the presence of the bacteria and determine its location within grapevine. Grapevine infected and un-infected with the bacteria were manually sectioned using a razor blade and the sections were submerged in FAA (20% ethanol. 2.5% (v/v) acetic acid. 2.5% (v/v) formaldehyde). The samples with FAA were vacuumed for 3 hours and remained for additional 20 h at RT and subsequently were transferred to 50% ethanol and kept in −20° C. till further analysis. The sections were dehydrated by sequence transfers to 80% and 100% ethanol and then submerged in hybridization buffer (20 mM Tris-HCl [pH 8.0], 0.9 M NaCl, 0.01% sodium dodecyl sulfate, 30% formamide) with ten pmol of fluorescent probes; Eub338 for general bacteria and specific for DLB (see, Table 1) for 4 hr in RT. The sections were then washed in PBS and visualized under an IX81Olympus FluoView500 confocal microscope. Specificity of the detection was confirmed using a no-probe control.

Bacteria as Bio-Agent Against *Phytoplasma*:

In order to examine the potential of the bacteria as bio-agent against phytoplasma, five repeats of healthy and phytoplasma-infected periwinkle and grapevine plantlets were inoculated with the bacteria and re-planted as described above. Plants were then grown for eight weeks, after which characteristics including shoot length, leaves lengths, number of internodes and dry weight were examined. The experiment was conducted in five replicates, with PBS as a control.

Field Trials:

A field experiment was conducted to study the effect of spraying the isolate on reduction of yellows symptoms in field grown vines.

Bacterial Application.

A chardonnay plot in the Golan Heights of 468 vines with 35% infection was divided into seven untreated and treated plots which were sprayed once every two weeks along the growing season (April-November). The plants were sprayed with 10% cell suspension plus 0.1% Tween20 app. 500 ml per plant using a wheeled sprayer with a 1.8 mm nozzle turbo gun (Achim Raz Ltd). None-sprayed plots served as control.

Detection.

The presence of the bacterium was examined 7 and 14 d from spraying by PCR analysis and isolation DLB from leaf samples. Sampled leaves were from the middle of the vine (two leaves from two vines per plot). Three hundred mg of petiole and blade base tissue was grounded for DNA extraction and 1000 mg from petiole and leaf blade base was grounded for cell isolation on nutrient agar medium (NA). The leaves were thoroughly washed with commercial soap under running water and additional sterilization by dipping in 70% ethanol following hypochlorite 1% and three washes in sterile water was done before cell isolation.

Assessment of the Effect in the Vineyard.

At harvest each vine was scored for disease severity using a qualitative scale form 0—asymptomatic to 4—severely symptomatic. Yield and no. of clusters and was measured for 148 vines from manually harvested sprayed and unsprayed vines. Pruning weight was measured during dormancy period. Must Brix, pH and berry weight were measured from randomly picked berries from 55 sprayed and unsprayed vines. Yield load for each vine was calculated as the ratio between yield and pruning weight.

Bacteria Introduction into Carrots Via Seed Coating:

Thirty untreated carrot seeds (Cv. Dordogne) were incubated in 10 mL of a 10^8 CFU/mL bacteria formulation for 2 h at room temperature. The formulation was then filtered and seeds collected, placed on absorbent paper, dried and then sown in 400 mL pots containing either perlite of potting soil. As a control, the same amount of seeds was incubated in a similar manner with sterile formulation. Seeds were allowed to germinate in the greenhouse under natural day light conditions and temperature range of 25-27° C. For each batch of treated seeds four pots were sown, two with perlite and two with potting soil and each pot contained six seeds.

Eighteen days post sowing two young leaves were taken of one seedling in each pot. DNA was extracted and followed by classical PCR with bacteria specific primers.

5-Hydroxymethyl-2-furaldehyde. In addition the compound Pyrrolo[1,2-a]pyrazine was identified by LC-MS analysis (data not shown).

TABLE 1

Primers and probes used

| | DNA region | Name | Sequence | SEQ ID NO: | Annealing Tm (° C.) |
|---|---|---|---|---|---|
| Primer | ITS | ITSX-f | GTTCCCGGGCCTTGTACACAC | 16 | 55 |
| | | ITSX-r | GGTTCTTTTCACCTTTCCCTC | 17 | 55 |
| | 16S rDNA | Dyella-f | CTCTGTGGGTGGCGAGTGGC | 18 | 63 |
| | | Dyella-r | ACCGTCAGTTCCGCCGGG | 19 | 63 |
| Probe | 16S rDNA | Dyella | Cy5-GCCACTCGCCACCCACAGAG | 20 | |
| | Bacteria 16S rDNA | EUB338 | Cy3-GCTGCCTCCCGTAGGAGT | 21 | |

Example 1

Isolation and Identification of the Bacterium of the Invention

Bacteria Isolation and Identification:

Plating homogenate of the planthopper on CV agar after surface sterilization resulted in growth of $7*10^5$ colony forming units with identical morphology. The 1421 bp long DNA sequence of the 16S rRNA gene showed 97% identity to *Dyella ginsengisoli* (accession No. EF191353) and *Frateuria aurantia* (accession No. CP003350) (Xanthomonadaceae), isolated from soil and plant, respectively. The identity of this isolate was confirmed by its internal transcribed spacer (ITS) sequence 877 bp long DNA sequence, which showed 84% identity to *Frateuria aurantia* (accession No. CP003350). These results indicate that the isolate is a new genus.

Bacterial Genome Analyses:

The bacteria's genome contains 4,191471 bp, with a G+C content of 68.6%. The mutual Effective Overlap Score between the bacteria and phytoplasma was 0, indicating that the growth capacity of both species is not dependent on common metabolites. A total of five potential clusters for secondary metabolites were identified in the bacteria genome including three bacteriocins clusters, one cluster of terpene and one cluster of NRPs.

Example 2

Antagonistic Effect of the Bacteria's Supernatant

Antagonistic Test of the Bacteria's Supernatant:

Filtrate of the bacteria'a supernatant inhibited spiroplasma development in vitro (FIG. 1).

Figure 2:
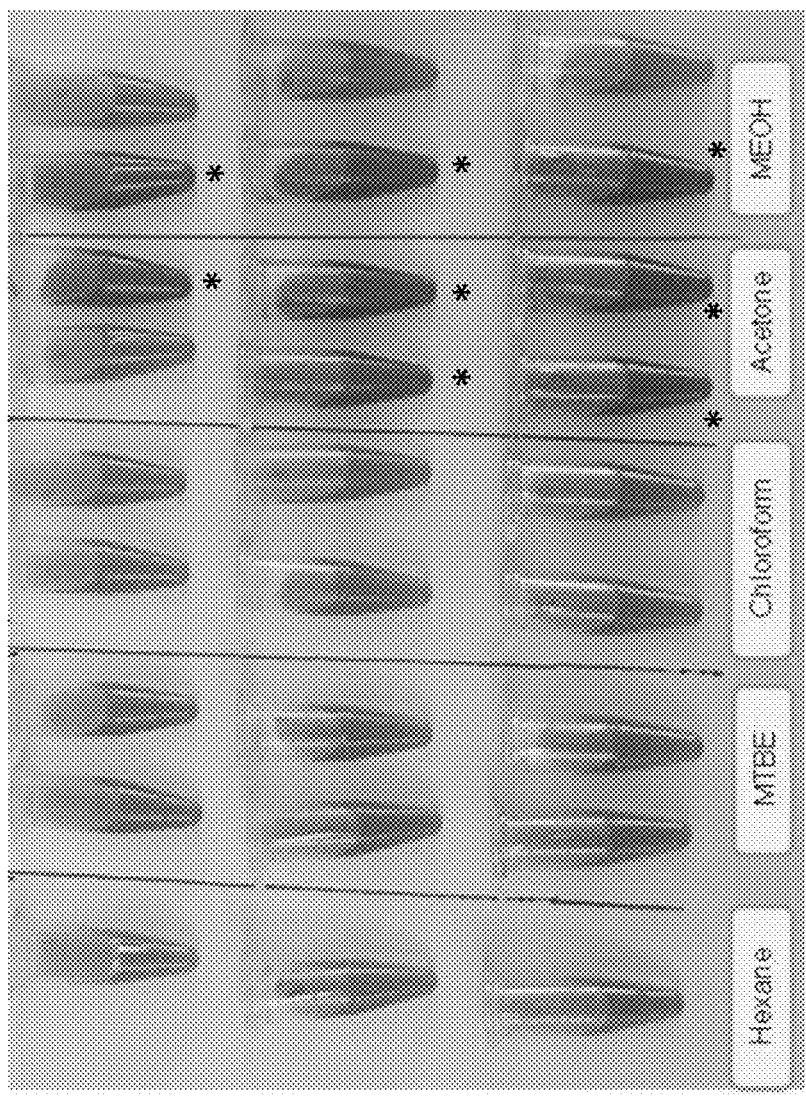
FIG. 2 illustrates the effect of fraction extract on spiroplasma growth of (from left to right) hexane, MBTE, chloroform, acetone, and MEOH. Bright medium indicates spiroplasma growth while the darker medium (marked by "*") indicates spiroplasma inhibition.

Identification of Active Fraction Extracts:

When the effect of each fraction extract on spiroplasma growth was assessed, only methanol and acetone extracts inhibited spiroplasma in vitro while none of the fractions obtained from sterile control medium inhibited this model bacterium (FIG. 2).

Figure 3:
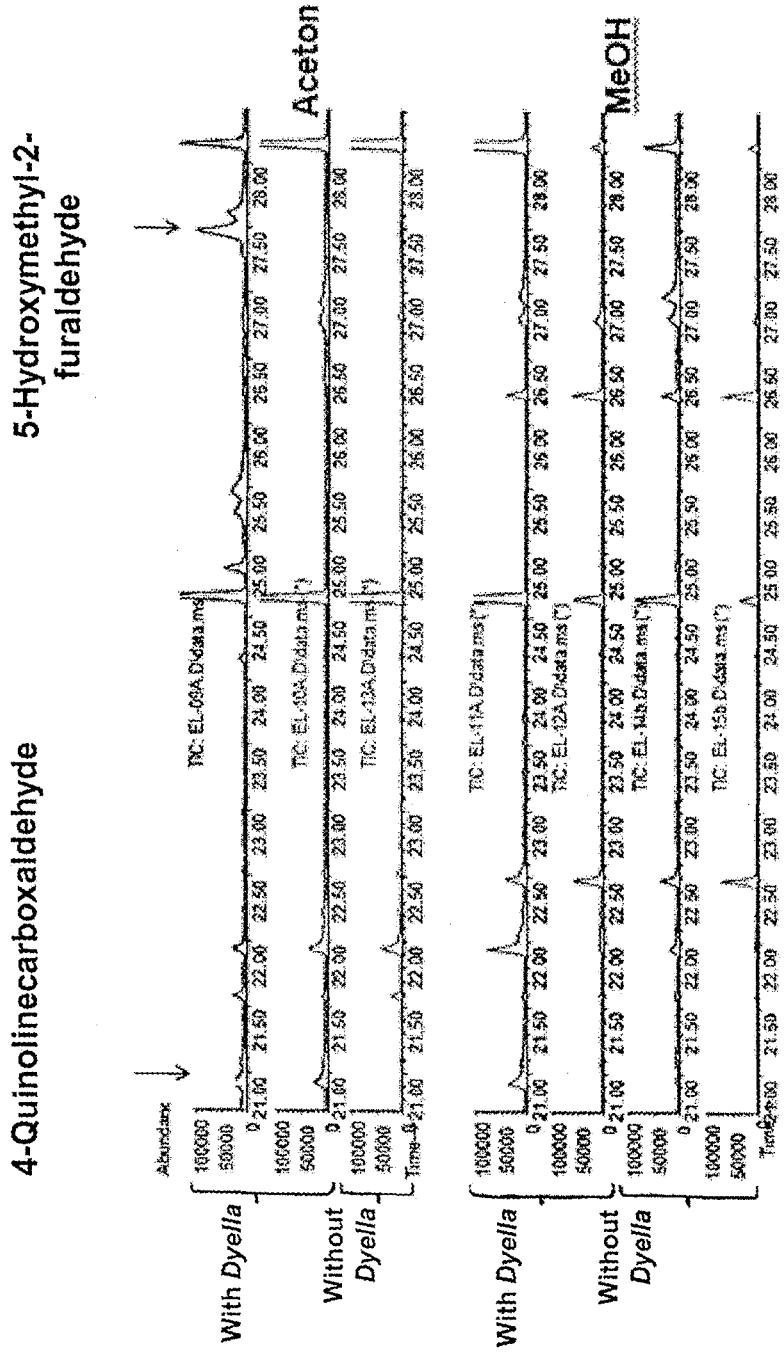
FIG. 3 demonstrates the gas chromatography-mass spectrometry (GC-MS) analysis on methanol and acetone fraction extract obtained from medium with and without DLB.
Figure 4B:
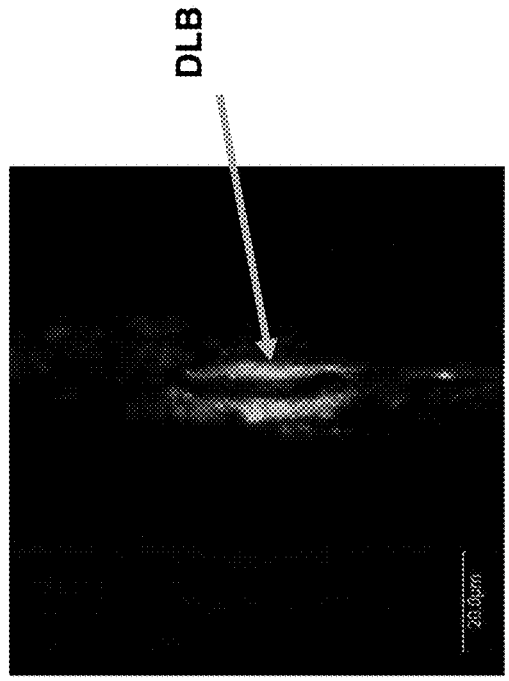
FIGS. 4A-D present FISH analysis of DLB location in grapevine plant petiole sections using different probes.
Figure 4D:
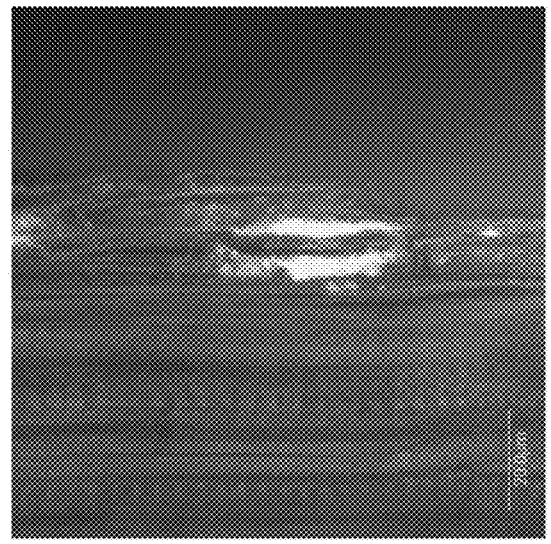
Figure 4A:
Figure 4C:
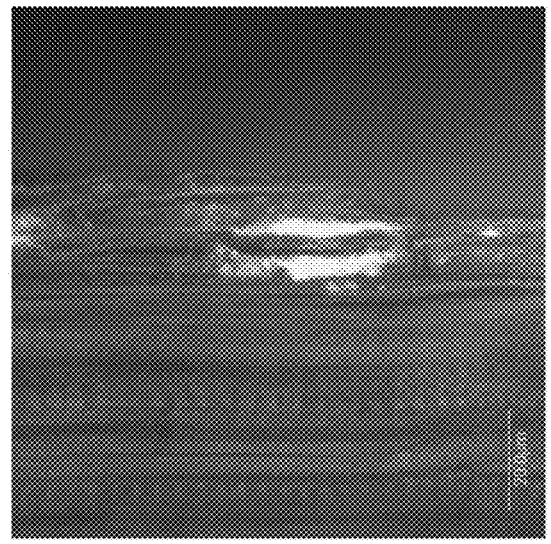
Figure 5A:
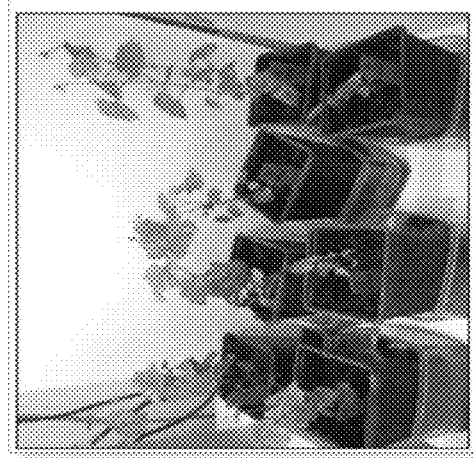
FIGS. 5A-E demonstrate the influence of DLB on grapevine plantlets eight weeks post inoculation.
Figure 5B:
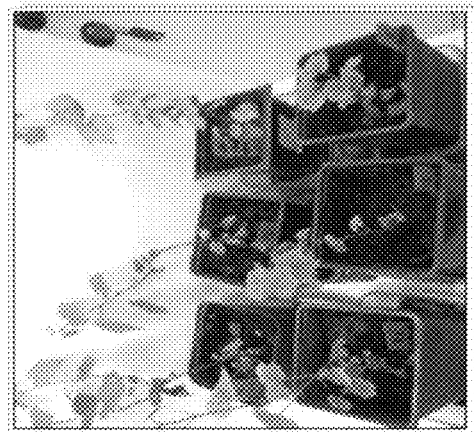
Figure 5C:
Figure 5D:
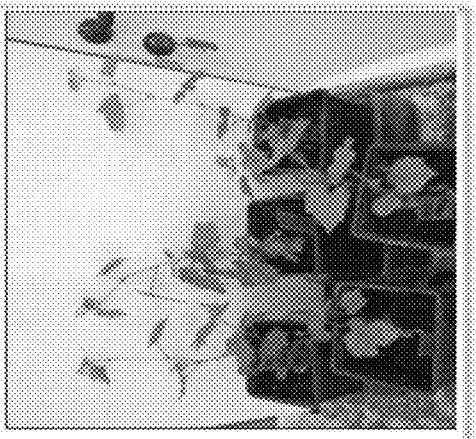
Figure 5E:
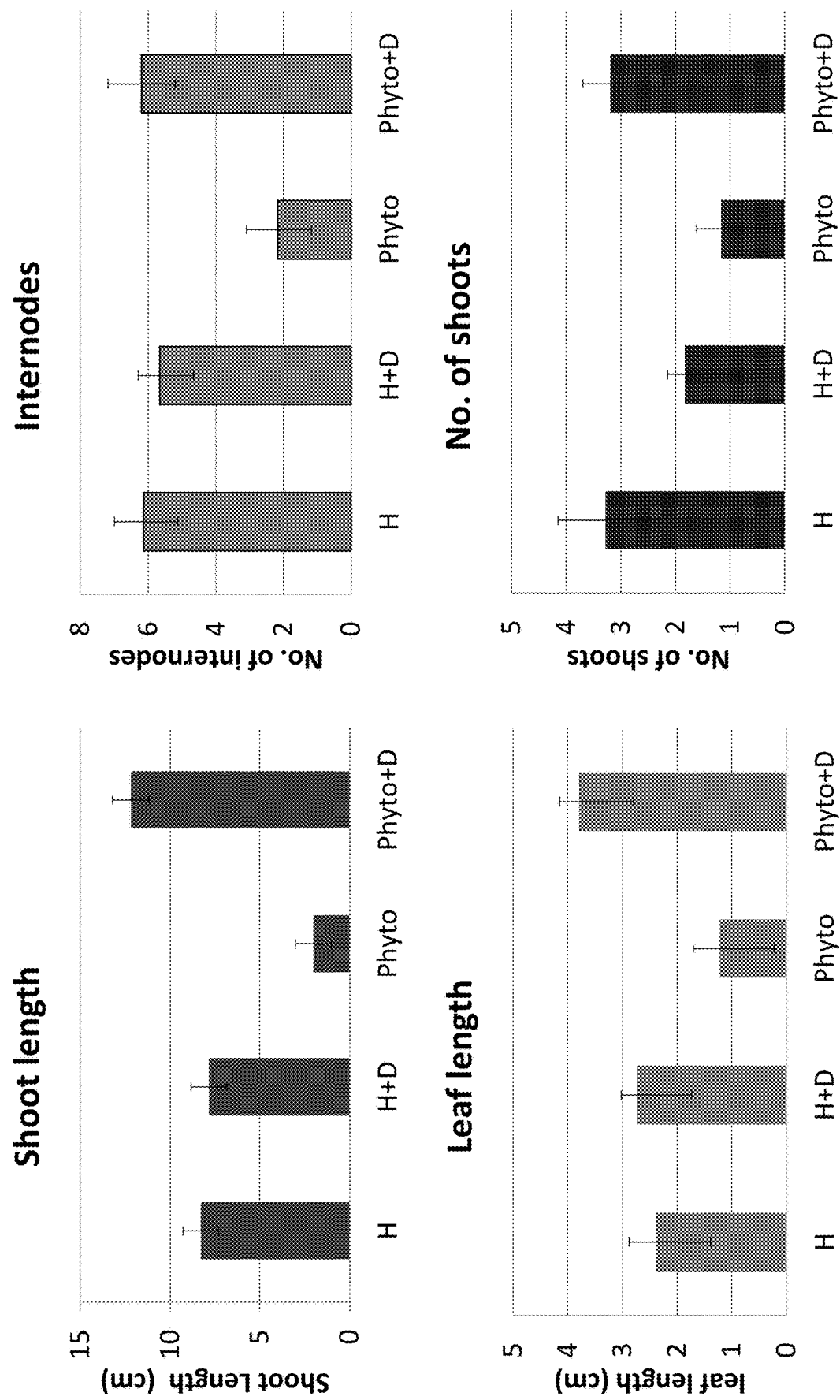
Figure 6B:
FIGS. 6A-E depicts the influence of DLB on periwinkle plantlets eight weeks post inoculation.
Figure 6D:
Figure 6A:
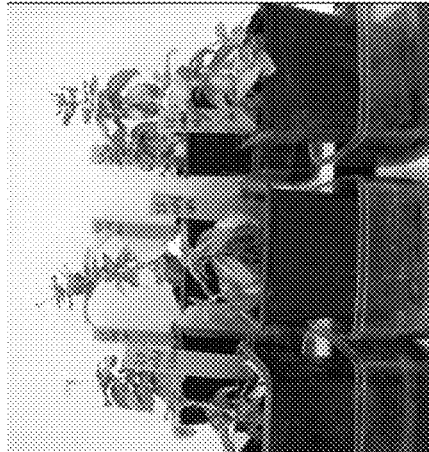
Figure 6C:
Figure 6E:
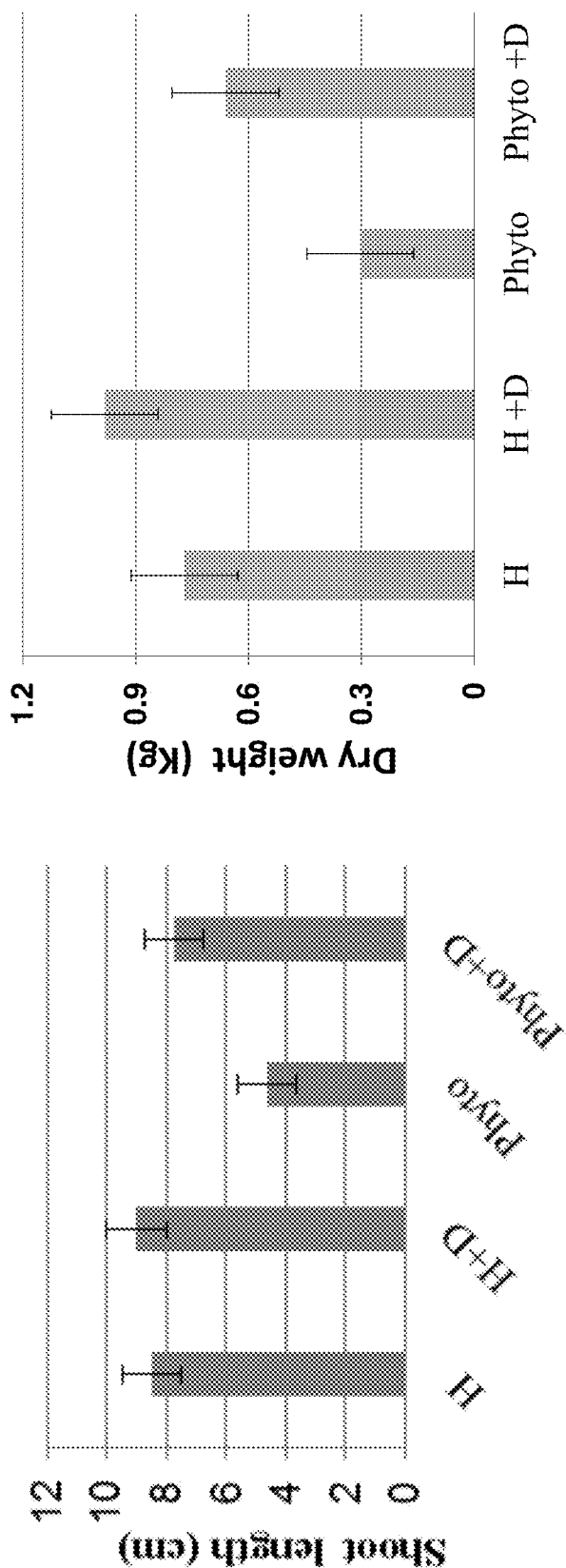

Volatiles Identification in *Dyella* Active Fraction Extracts:

By comparing the pattern of volatiles in the active fraction extracts (methanol and acetone) to the same fraction extract of the sterile control medium—two compound were identified as potential inhibitory against spiroplasma (FIG. 3). These compounds were 4-Quinolinecarboxaldehyde and 5-Hydroxymethyl-2-furaldehyde. In addition the compound Pyrrolo[1,2-a]pyrazine was identified by LC-MS analysis (data not shown).

Antagonistic Test:

Only 4-Quinolinecarboxaldehyde was able to inhibit *Spiroplasma* growth at the concentration of 1 milimolar, while no inhibition was shown in the presence of 5-Hydroxymethyl-2-furaldehyde at the same concentration.

Example 3

Bacteria Detection in Plants After Inoculation

PCR.

The bacteria was able to penetrate plantlets by all methods examined including spraying, petting leafs, injection to the stem and root submergence in bacterial culture. However, the best inoculation was achieved by leaf spraying reaching up to 73% of the plants were inhabited by the bacteria a week after spraying. the bacteria was able to move in the plant up to 28 cm (3 internodes) but most of the samples showed that it remained in the first internode it was injected to. Examination the presence of the bacteria in inoculated plantlets by specific PCR showed that the bacteria occupied the new emerging leaves of grapevine plants three weeks post inoculation while no PCR product was detected in the non-inoculated plants. In addition, six weeks post inoculation the bacteria could not be detected in any of the plants.

Microscope.

Observations on the bacteria culture showed that this bacterium is a 1 μm long rod shape. The FISH analysis showed that the bacteria was restricted to the phloem of grapevines two weeks post bacteria-inoculation (as shown in FIG. 4).

Bacteria as Bio-Agent Against *Phytoplasma:*

No significant differences were observed between the healthy control plants and those inhabited by the bacteria. When the bacteria was introduced to phytoplasma-infected plantlets the influence of the phytoplasma on the plant was significantly reduced, as can be seen by all recorded parameters (shoot length, leaves lengths and internodes) observed eight weeks post inoculation (FIGS. 5A-E).

Similar results were observed when the bacteria was introduced to periwinkle: no significant differences in healthy plant characteristics but the bacteria presence in phytoplasma-infected periwinkle reduced the effect of phytoplasma on these plants in terms of shoots length and dry weight, as was measured eight weeks post inoculation (FIGS. 6A-E).

Example 4

Field Experiments

Figure 7D:
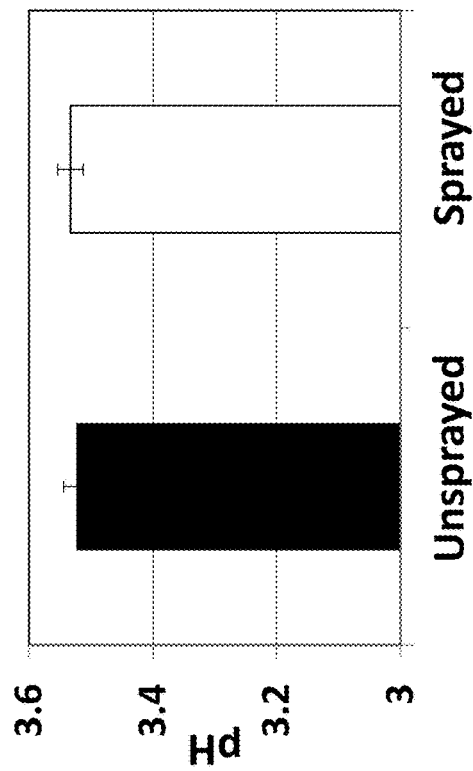
FIGS. 7A-D present bar graphs showing the influence of DLB application on grapevines.
Figure 7C:
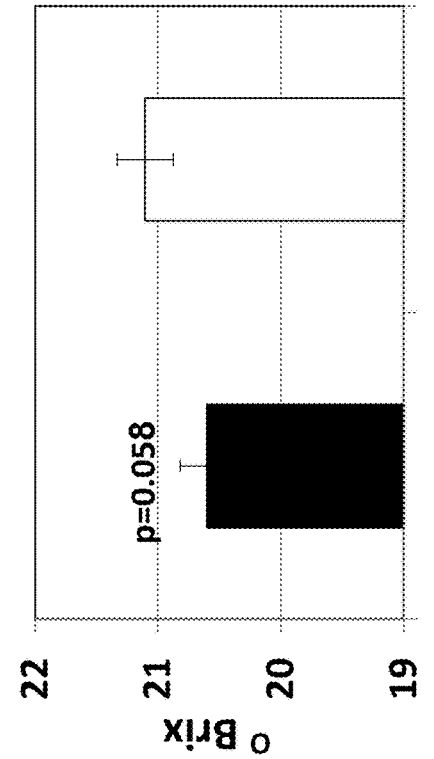
Figure 7A:
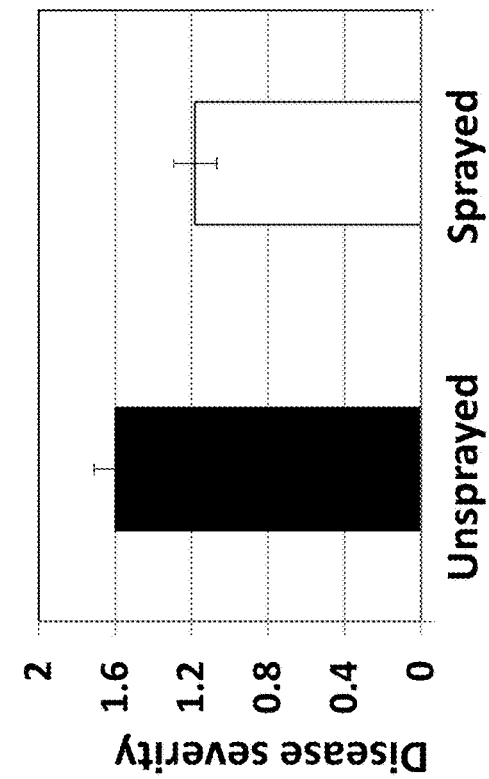
Figure 7B:
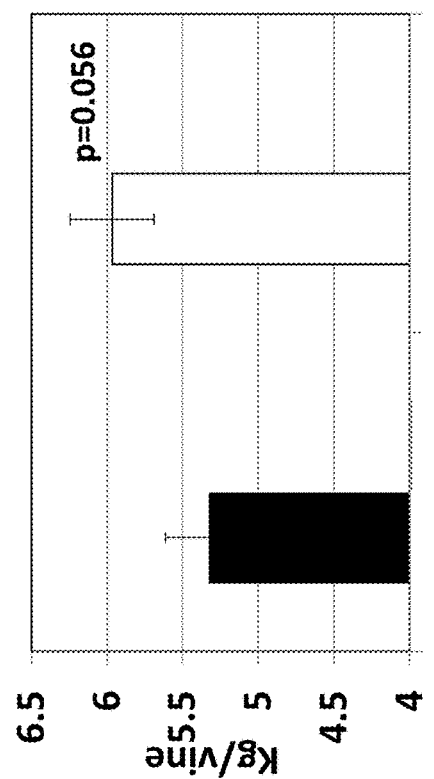

Spraying with 10% suspension resulted in the highest rate of penetration into the leaves improved by addition of a surfactant. The bacteria was detected in sprayed samples 7 days post introduction (dpi) in 9/17 and 7/17 sampling dates by PCR and cell isolation methods respectively. Positive results ranged 2-85%. The bacteria was present in the leaves mostly 5-8 dpi but up to 15 dpi. In sprayed vines, symptom severity was reduced by 25% (FIG. 7A), yield was increased by 12% (FIG. 7B), and rate of symptom remission increased by ca. 20% compared to control. Sugar level was higher by 0.5 Brix but no difference in pH was detected (FIG. 7C, D). Yield load of sprayed vines increased significantly in sprayed vines and healthy vines but not in severely infected (FIG. 8A, B, D).

To summarize, a bacterium was isolated from the planthopper vector of grapevine phytoplasma. This bacterium is most closely related to *Dyella ginsengisoli*, but may prove to be a separate genus. The bacterium was able to penetrate plants by both roots and leaves, settle in the phloem for at least three weeks, and its presence seems to affect the morphology of the phytoplasma-infected plants but not the healthy ones. In some parameters, the effect of phytoplasma on plant morphology was markedly reduced. Field experiments supported lab observations. The results indicate that the bacteria possess the ability to migrated from treated seeds to the seedling.

Example 5

Bacteria Substrate Characterization

The inventors of the present invention analyzed and characterized the bacterium's growth substrate. Table 2 shows the DLB antibiotic susceptibility test (29 antibiotics tested).

The bacterium is resistant to the following antibiotics: nitrofuration, ciprofloxacin, cephalothin, meropenem, norfloxacin, nalidixic acid, colistinsulfate, imipenem, cefeprime, aztreonam and cefuroxime (11 out of 29 tested antibiotics, Table 2).

TABLE 2

DLB antibiotic susceptibility test.

| Antibiotic (type) | Inhibition cycle diameter (mm) | Antibiotic (type) | Inhibition cycle diameter (mm) |
|---|---|---|---|
| nitrofuration | 2 | neomycin | 10 |
| ceftriaxone | 10 | colistinsulfate | 2-3 |
| tetracycline | 10 | imipenem | 2-3 |
| gentanicin G | 10 | polymyxin-B | 10 |
| ampicilin A | 10 | amoxycillin | 10 |
| ciprofloxacin | 2 | carbencillin | 10 |
| kanamycin | 10 | tobaramycin | 10 |
| cephalothin | 2 | sulphamethoxazole | 10 |
| streptomycin | 10 | trimethoprime | 10 |
| chloramphenicol | 10 | cefeprime | 1 |
| meropenem | 1 | aztreonam | 1 |
| norfloxacin | 2 | vancomycin | 10 |
| nalidixic acid | 1 | cefuroxime | 1 |
| amikacin | 10 | ticarcillin | 10 |
| piperacillin | 10 | | |

DLB Metabolism:

The environmental metabolites that can be utilized by DLB were determined using the BD BBL™ Crystal™ En/non-fermenters kit. The results show the metabolites the bacterium uses or does not use (Table 3 and 4, respectively):

TABLE 3

| Sugar/Sugar derivatives | Amino acids | Others |
|---|---|---|
| Arabinose | Proline nitroanilide | p-n-p-xyloside |
| Mannose | γ-L-glutamyl p-nitroanilide | Esculine |
| Sucrose | Phenylalanine | Urea |
| Melibiose | Glycine | |
| Galactose | Arginine | |
| Inositol | | |
| p-n-p-α-β-glucoside | | |

TABLE 4

| Sugar/Sugar derivatives | Amino acids | Others |
|---|---|---|
| Rhamnose | Lysine | p-nitrophenyl phosphorylcholine |
| Sorbitol | | p-nitrophenly β-glucuronide |
| Mannitol | | p-nitrophenyl-N-acetyl Glucosaminide |
| Adonitol | | Citrate |
| p-nitrophenyl phosphate | | Malonate |
| p-nitrophenyl β-galactoside | | Tetrazolium |
| p-nitrophenyl bis-phosphate | | |
| p-nitrophenyl α-arabinoside | | |

Example 6

Inhibition of *Spiroplasma* by Substances Secreted by the Bacterium of the Invention Antagonistic activities of substances secreted by DLB on phytoplasma cannot be tested directly because of the inability to cultivate phytoplasmas in artificial medium. For this reason, the potential inhibition of these substances was tested on *Spiroplasma melliferum*, a cultivable Mollicute. The experiment was conducted in a 96-wells microplate. 150 μl fresh broth containing phenol red and 4 μl spiroplasma cells (app. $10^5$ cells) were added to each well. Three compounds were chosen based on the analysis that showed they are secreted by DLB, and their synthetic equivalents were used in the experiment: Quinolinecarboxaldehyde, Hydroxymethyl-2-furaldehyde and Pyrrolo[1,2-a]pyrazine (Sigma-Aldrich, USA) were added in different concentrations (2-0.02 mM) to the inoculated medium in five replicates. The microplate was incubated for two days at 28° C. and the color of the medium was scored by a plate-reader (Multiskan EX, Thermo scientific, Waltham, Mass. USA) at OD=595 nm. *Spiroplasma* growing in fresh broth served as a positive control, medium without spiroplasma served as a negative control and the inhibitory effect of oxy-tetracycline in different concentrations was used as a reference.

Figure 9:
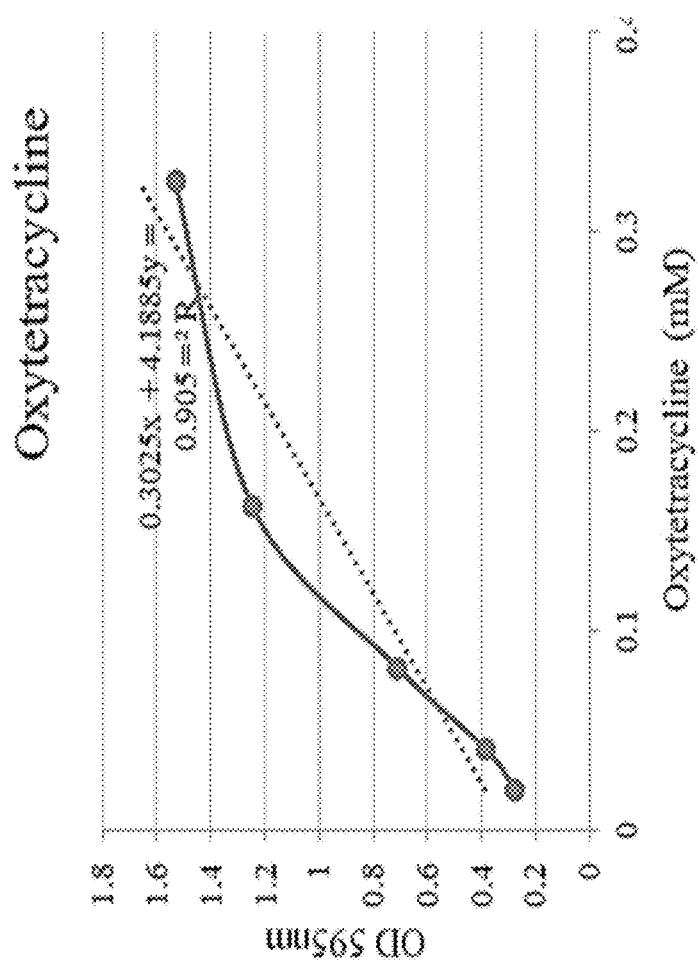
FIG. 9 presents a graph showing the standard curve of reference antibiotics—oxytetracycline.

In addition to scoring each substance separately, the combination of these three substances was tested by adding different concentrations (2-0.02 mM each) of two compounds to the same well. The minimum inhibitory concentration (MIC) of oxytetracycline was 0.35 mM (FIG. 9).

Figure 10:
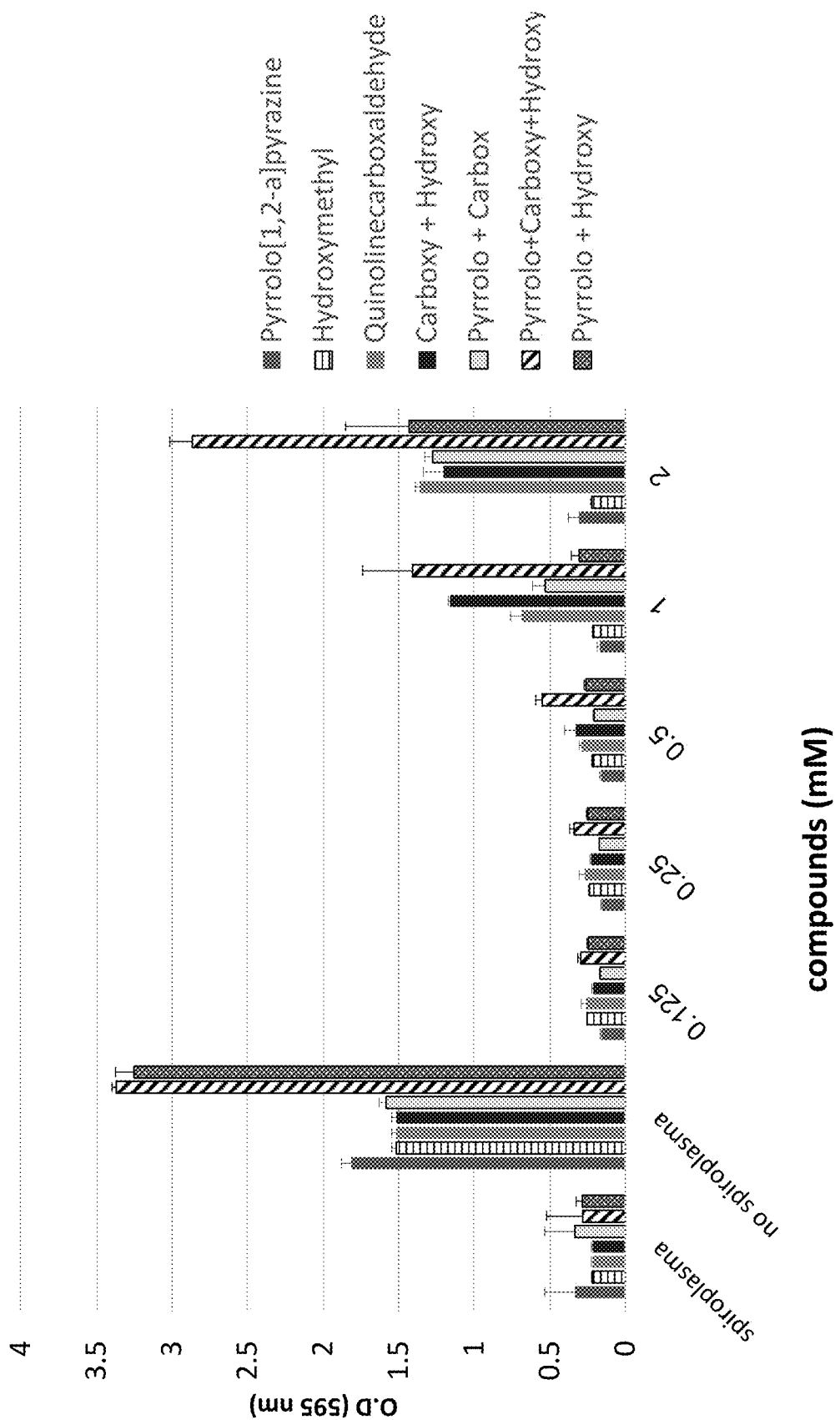
FIG. 10 presents a graph showing the effect of different substances in different concentrations on spiroplasma growth, as was measured by microplate test.
Figure 11:
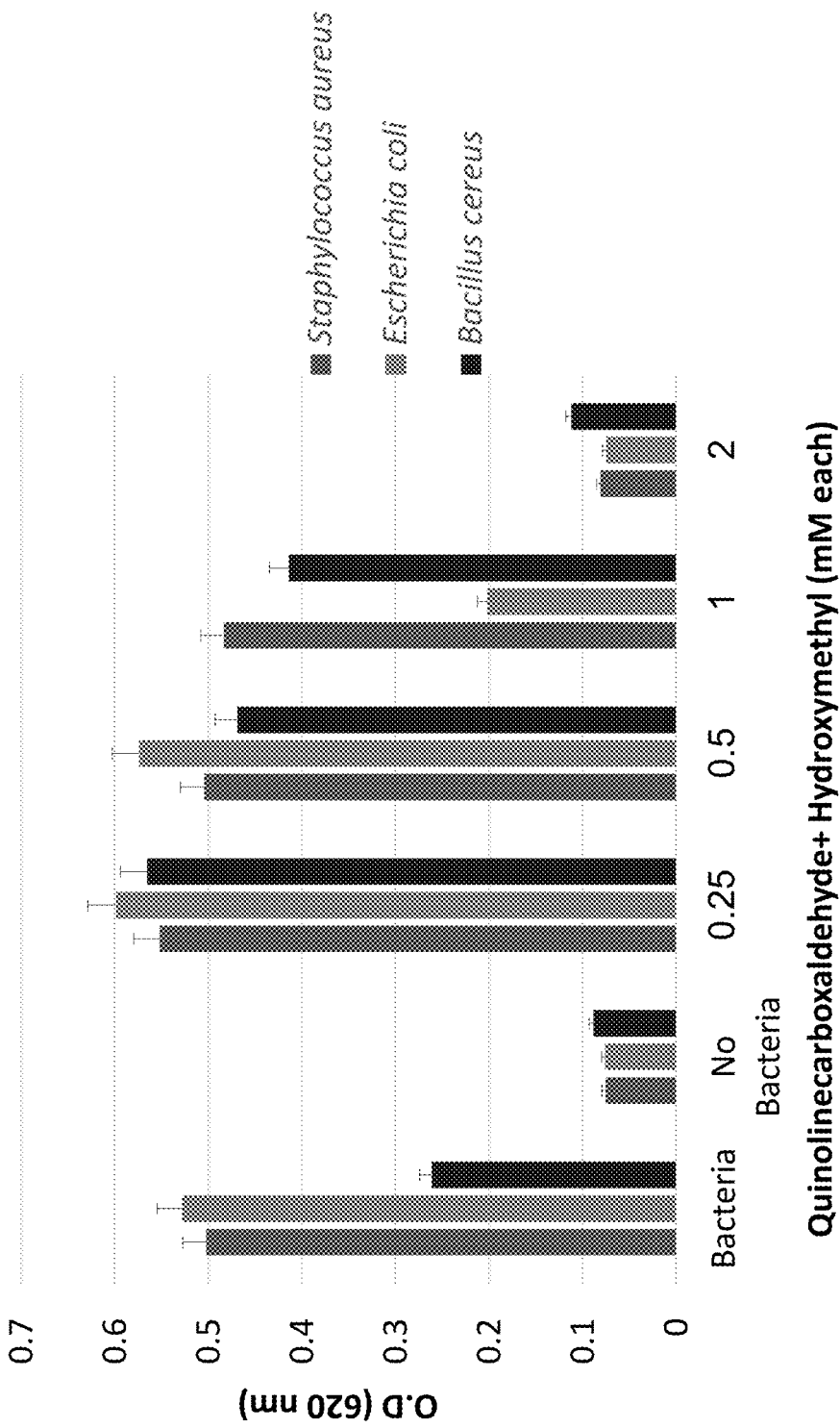
FIG. 11 is a bar graph showing different concentrations of Quinolinecarboxaldehyde with Hydroxymethyl and their effect on several bacterial species, as was measured by microplate test. In each triplet of bars, the left column represents *S. aureus*, the middle column represents *E. coli*, and the right column represents *B. cereus*.

Quinolinecarboxaldehyde inhibited spiroplasma growth at concentrations 2 and 1 mM while Pyrrolo[1,2-a]pyrazine inhibit spiroplasma at 2 mM only. No inhibition was shown by Hydroxymethyl-2-furaldehyde at the concentrations examined. Combination of Quinolinecarboxaldehyde with either Pyrrolo or Hydroxymethyl did not show significant impact at 2 mM but influenced spiroplasma inhibition at 1 mM (FIG. 10). The combination of Pyrrolo[1,2-a]pyrazine with Hydroxymethyl changed the medium absorption (see control Pyrrolo with Hydroxy) and therefore the inhibition measurement is not valid.

In conclusion, synthetic compounds equivalent to the substances secreted by DLB varied in their effect on spiroplasma growth—a model bacterium for phytoplasma. The most efficient compound was Quinolinecarboxaldehyde but its minimum inhibitory concentration (MIC) is still higher than the reference antibiotics—oxytetracycline.

The combination of this compound with Pyrrolo[1,2-a]pyrazine showed an antagonistic effect at 1 mM, suggesting that spiroplasma inhibition was significantly lower in the presence of these two compounds together than with only Quinolinecarboxaldehyde.

The combination of Quinolinecarboxaldehyde with Hydroxymethyl showed a synergistic effect at 1 mM, suggesting that spiroplasma inhibition in the presence of these two compounds together was significantly higher than spiroplasma inhibition with only Quinolinecarboxaldehyde.

The effect of Quinolinecarboxaldehyde with Hydroxymethyl combination, that inhibited the spiroplasma, was examined on different bacterial species: *Staphylococcus aureus, Escherichia coli* and *Bacillus cereus*. These strains were examined in 96-wells microplate. 150 µl LB medium and 4 µl bacteria cells (app. 105 cells) were added to each well. The microplate was incubated for one day at 37° C. and the turbidity was scored by a plate-reader (Multiskan EX, Thermo scientific, Waltham, Mass. USA) at OD=620 nm. Bacteria growing in fresh broth served as a positive control, medium without bacteria served as a negative control.

The bacterial species examined were inhibited at 2 mM, while only *Escherichia coli* was effected at 1 mM.

Example 7

Inhibition of *Ca. Liberibacter*

*Ca. Liberibacter* is a genus of Gram-negative bacteria comprising of several economically important plant pathogens. Of which, *Ca. L. asiaticus* and *Ca. L. solanacearum* are the suspected causal agents of the devastating citrus greening (Haunglongbing-HLB) and zebra chip/carrot yellows diseases, respectively. Similar to *Ca.* phytoplasma phytopathogens, *Liberibacter* are also vector transmitted (by psyllids) and reside exclusively in the plant phloem tissue. Due to these similar characteristics and others, the inventors of the invention explored the potential use of DLB as a bio-agent against diseases caused by *Ca. Liberibacter*, focusing on carrot yellows caused by *Ca. L. solanacearum*.

Different sets of real-time PCR primers are designed based on the genome sequence of DLB. These primers are first tested on serially diluted purified DNA to determine primers sensitivity. The most sensitive primer is tested using DNA extractions from infected periwinkle plants to determine its efficacy and specificity.

The application of DLB is performed by either irrigation or by spraying and thereafter the most efficient application method is determined using real-time PCR. The DLB spread and abundance in different plant tissues is then determined in respect to application method using real-time PCR. The DLB longevity is determined in carrot plants in respect to the application method using real-time PCR.

DLB are applied to carrots (according to the optimized procedure above) challenged with hot psyllid vectors. Symptom appearance and *Candidatus Liberibacter* solanacearum (Lso) titer is scored over time compared with carrot plants not treated with DLB.

To determine the effect of DLB on psyllid plant colonization, plants are inoculated according to the optimized protocol above and then psyllids (clean or hot) are introduced into small net cages, Psyllids survival, number of laid eggs and nymph survival. To determine the ability of psyllids to take up DLB from carrot and transmit it, carrot plants are inoculated with DLB and its establishment in the plant is verified using real-time PCR. Then, clean psyllids are allowed to feed on the infected plants for 2 days and then are tested by real-time PCR for the presence of Lso in their body.

In additional exemplary procedures, these psyllids are then placed on clean carrot plants allowing feed for 4 days. Inoculated plants are tested over time for the transmission of DLB into carrots using real-time PCR.

In additional exemplary procedures, Lso-infected psyllids are allowed to feed either on clean carrot plants or Lso infected plants. The titer of Lso inside the psyllid is determined over time using real-time PCR.

Specifically, carrot plants at the 3-4 true leaf stage were sprayed until runoff or irrigated with 50 mL formulation of DLB with a concentration of 10^8 CFU/mL. Carrot plants were then sampled 3, 7, 10 and 16 days post inoculation to determine DLB presence in the leaves. Half a gram of newly emerging leaves was used for DNA extraction followed by PCR with DLB specific primers. Results are presented in table 5 below.

TABLE 5

| Days post inoculation | Inoculation method | DLB positive by PCR (%) | Number of samples |
|---|---|---|---|
| 3 | Spraying | 100 | 7 |
| 3 | Irrigating | 60 | 5 |
| 7 | Spraying | 87.5 | 8 |
| 7 | Irrigating | 40 | 6 |
| 10 | Spraying | 85 | 8 |
| 10 | Irrigating | 0 | 7 |
| 16 | Spraying | 37.5 | 8 |
| 16 | Irrigating | 0 | 6 |

Example 8

*Xanthomonas* Pathogenesis Assay

Sesame plants (4 weeks old) were exposed to either DLB or DH5α (*E. coli*) bacteria by rubbing leaves with a cotton swab immersed with bacterial culture. The plants were then incubated for 5 days at room temp to allow DLB penetration.

A culture of two strains of the phytopathogenic bacterium *Xanthomonas campestris* (depicted "Xcc" and "Xcv", respectively) was prepared (O.D. 595 nm=0.3). A small puncture was made with a needle on one of the upper sesame leaves, and a drop of the bacterial culture was placed on the leaf's puncture area. After 3 days the assay was terminated and symptoms (such as lesions) were recorded.

Figure 12:
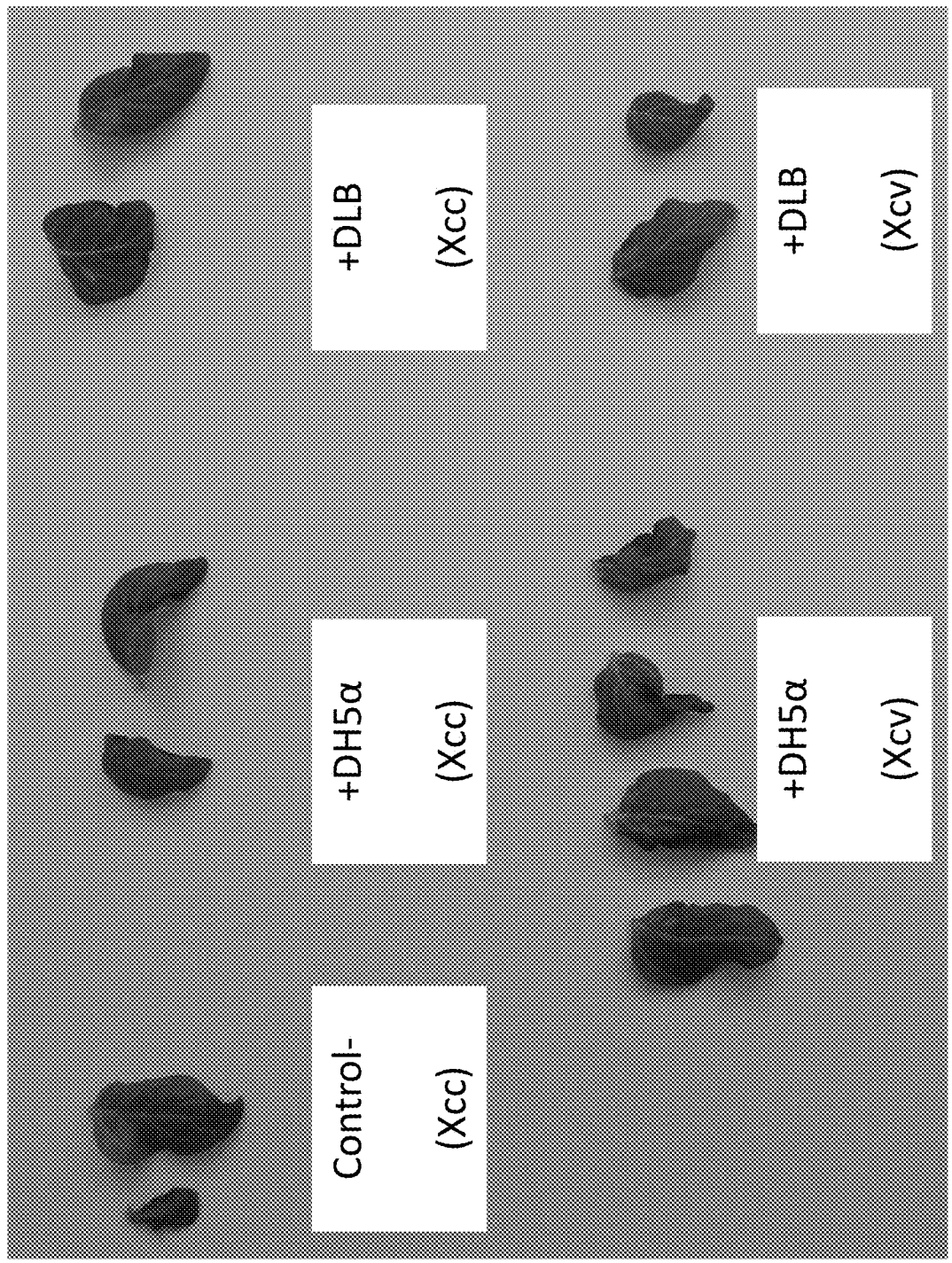
FIG. 12 depicts the effect of the bacterium of the invention under a *Xanthomonas* pathogenesis assay.

The results show that the presence of DLB reduces the damage of a pathogenic bacterium which is not restricted to phloem (see, FIG. 12).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of treating or reducing a symptom of a pathogen selected from the group consisting of: *Candidatus Liberibacter, Xanthomonas campestris, Spiroplasma melliferum* and *Phytoplasma solani*, the method comprising the step of contacting a pathogen, a plant or a plant part with an isolated bacterium comprising a nucleic acid sequence having at least 98% sequence identity to: SEQ ID NO: 1 and at least one additional nucleic acid sequence having at least 85% sequence identity to any one of SEQ ID NO: 2-14, thereby treating or reducing the symptoms of the pathogen.

2. The method of claim 1, wherein said symptom results in damage to a plant or plant part.

3. The method of claim 1, wherein said symptom comprises: leaf discoloration, a plant part necrosis, leaf curling, lack or incomplete lignifications of a shoot, inflorescence abortion.

4. The method of claim 1, wherein said symptom is related to: callose deposition, degeneration of the phloem or both.

* * * * *

SEQUENCE LISTING

<160> NUMBER OF SEQ ID NOS: 21

<210> SEQ ID NO 1
<211> LENGTH: 1421
<212> TYPE: DNA
<213> ORGANISM: Dyella-like bacterium
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (682)..(682)
<223> OTHER INFORMATION: n is a, c, g, or t
<220> FEATURE:
<221> NAME/KEY: misc_feature
<222> LOCATION: (691)..(691)
<223> OTHER INFORMATION: n is a, c, g, or t
<220> FEATURE:
<221> NAME/KEY: misc_feature
<222> LOCATION: (784)..(784)
<223> OTHER INFORMATION: n is a, c, g, or t
<220> FEATURE:
<221> NAME/KEY: misc_feature
<222> LOCATION: (841)..(841)
<223> OTHER INFORMATION: n is a, c, g, or t
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (1391)..(1391)
<223> OTHER INFORMATION: n is a, c, g, or t
<220> FEATURE:
<221> NAME/KEY: misc_feature
<222> LOCATION: (1396)..(1396)
<223> OTHER INFORMATION: n is a, c, g, or t
<220> FEATURE:
<221> NAME/KEY: misc_feature
<222> LOCATION: (1413)..(1413)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t

<400> SEQUENCE: 1

```
acatgcaagt cgaacggcag cacagcagan cttgctctgt gggtggcgag tggcggacgg    60
gtgagtaatg catcgggacc tacccagacg tggggataa cgtagggaaa cttacgctaa   120
taccgcatac gtcctacggg agaaagcggg ggatcttcgg acctcgcgcg gttggacgga   180
ccgatgtgcg attagctagt tggtgaggta atggctcacc aaggcgacga tcgctagctg   240
gtctgagagg atgatcagcc acactgggac tgagacacgg cccagactcc tacgggaggc   300
agcagtgggg aatattggac aatgggcgca agcctgatcc agcaatgccg cgtgtgtgaa   360
gaaggccttc gggttgtaaa gcacttttat caggagcgaa acgctgtcgg cgaatacccg   420
gcggaactga cggtacctga ngaataagca ccggctaact tcgtgccagc agccgcggta   480
atacgaaggg tgcaagcgtt aatcggaatt actgggcgta aagcgtgcgt aggcggttgt   540
ttaagtctgc tgtgaaaccc cgggctcaac ctggaatgg cagtggatac tgggcagcta   600
gagtgtgata gaggatggtg gaattcccgg tgtagcggtg aaatgcntag agatcgggag   660
```

```
gaacatcagt ggcgaaggcg gnccatctgg ntcaacactg acgctgaggc acgaaagcgt    720
ggggagcaaa caggattaga taccctggta gtccacgccc taaacgatgc gaactggatg    780
ttgntctcaa ctcggagatc agtgtcgaag ctaacgcgtt aagttcgccg cctggggagt    840
ncggtcgcaa gactgaaact caaaggaatt gacgggggcc cgcncaagcg gtggagtatg    900
tggtttaatt cgatgcaacg cgaagaacct tacctggcct tgacatgtct ggaatcctgc    960
agagatgcgg gagtgccttc gggaatcaga acacaggtgc tgcatggctg tcgtcagctc   1020
gtgtcgtgag atgttgggtt aagtcccgca acgagcgcaa cccttgtcct tagttgccag   1080
cacgtaatgg tgggaactct aaggagactg ccggtgacaa accggaggaa ggtgggatg    1140 acgtcaagtc atcatggccc ttacggccag ggctacacac gtactacaat ggtcggtaca   1200
gagggttgca atgccgcgag gtggagccaa tcccagaaag ccgatcccag tccggatcgt   1260
agtctgcaac tcgactacgt gaagtcggaa tcgctagtaa tcgcagatca gctatgctgc   1320
ggtgaatacg ttcccgggcc ttgtacacac cgcccgtcac accatgggag tgagttgctc   1380
cagaagccgt nagccnaacc gcaagggggg cgncgaccnc g                       1421

<210> SEQ ID NO 2
<211> LENGTH: 877
<212> TYPE: DNA
<213> ORGANISM: Dyella-like bacterium
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (871)..(871)
<223> OTHER INFORMATION: n is a, c, g, or t

<400> SEQUENCE: 2
gccgttagcc taaccgcaag gggggcgacg accacggagt ggttcatgac tggggtgaag     60
tcgtaacaag gtagccgtat cggaaggtgc ggctggatca cctcctttcg agaaaggcag    120
catcactgct gcaagacgtc cacacaagac acctgcacat ccgcacgcca ccaggcgtga    180
gagcccaaag ggctcatgaa gctttatggg tctgtagctc aggtggttag agcgcacccc    240
tgataagggt gaggccggtg gttcgagtcc tcccagaccc accactttgg ggccatagct    300
cagctgggag agcacctgct ttgcaagcag ggggtcgtcg gttcgatccc gactggctcc    360
accagttagt gacggatgtg tagcgcacac aaaagatttt agagagccgg cggcgttgag    420
gccgtttggc tgttctttga aaatgtaaac gagtgacaag cgttttggtt cgaaaccgaa    480
ccgagatgtg tcgttgaggc aacggcgatg cgtcgtttgg cataacttcg aggcgacttg    540
gggttatatg gtcaagcgac caagcgtata cggtggatgc cttggcggtc agaggcgatg    600
aaggacgtgg cagcctgcga aaagtgtcgg ggagctggac acaagctttg atccggcaat    660
gtccgaatgg ggaaacccac cgcgtaagcg gtatcgtgca gtgaattcat agctgtacga    720
agcgaacccg gggaactgaa atatctnagt acccggnaga aaagaaatca accgagattc    780
cctcagtagc gacnagcgaa cggggagtag cccaaaagcg cacgatgttt tagtcgaacg    840
```

```
                    gtctggaaag tccggccata gcgggtgata ncccccgt                      877
```

<210> SEQ ID NO 3
<211> LENGTH: 1254
<212> TYPE: DNA
<213> ORGANISM: Dyella-like bacterium

<400> SEQUENCE: 3

```
atgggttcct cgttcatcac tgggaaccag aacaccgtca ctggcaagct cggcacgctg       60
gcaatctaca acggccaaga taatacagtg accatgtcag atggtgccag cgtttccatt      120
tcgggtacat ccaaaaacaa tacaatcaac ctatcaagag gaagcttctc cgtatctgga      180
gcggatgcgt cagcactagc agctaccatt aatggatcaa acaataccaa tagctatgtg      240
tacgccggta tttacagcct aaatggtgac gggaatgcag ttaacgtgca gagtgcatca      300
gccgtcctaa atgtccacgg ctcgtcgaat ttattcaacg gaaataatgg gactatcaat      360
ttgttgtctg cgacaacac  aacggtcgcg acgtttgggt gcactgtgga cgcgacggca      420
gtaaactccg cagcattcac gggcaattcc gagacgatta aggtcgctga agggagcttc      480
tccctcagtg gttcgtcgag taccttcacg ggcactggaa cgacaacact gacagttggc      540
ggtaactcca acacgattaa tgagtcagcg aaatcgaccc tgacgatcac cggtgattac      600
aacataatca ccgacagtgc cggctcgtcg atttccgttg gtggcgaagg aaacagcgta      660
tccgaatcaa tgggtacgac catgaatgtc ggcggatcgg ataacaccgt tcatgttgga      720
gatcagtcga tacttcattt atctggcagc tcgaacaaaa tctatgcgag caactcgatc      780
atctatgttg ccgatggcac cactgtctcc atcttcggtt ccaatgacca ggtcattggt      840
ggcaccaacg atcacgtttc tgtaacaggc actaatgttt ccgttactgc ctcaaacagc      900
tgggtcggct tcgttggtga caataccggc gataccgtcg tcggtcccgg ggataccggc      960
tcaaactggt ccgctcccga ccccgatctc ccgcctgggg ataatggtgg atacacacca     1020
ccgcagacaa ccgctactct tcaagcaatg aatgtctcca ccccggtcgg gatgggggta     1080
gagatgcaga tgaaagactc cttggcagtc tcaggcatag cgtatgcgcc tgatgtacaa     1140
gccctcattc atgcgttgtc ggcgttcggt ggatcctttg caagcggaga tggggctctg     1200
gtgatctcgc cttcggctga agcaaatcac ttgcacctcg cagtggtagc ataa           1254
```

<210> SEQ ID NO 4
<211> LENGTH: 1359
<212> TYPE: DNA
<213> ORGANISM: Dyella-like bacterium

<400> SEQUENCE: 4

```
atgctgtcgg atcgagagat cgaagcggta cgcgagaagt acgaccgcag ccccgagtgg       60
gccgcctcga tgcactcaag gaaccgagag ggccagcagc agctagccaa gcatctcgcc      120
caagccgatg aggaccgcca gcggaccat  ctggcgacgg atgggaccgc atttcagatc      180
gaggcatttg gccgcgagaa ggtgtcgaag gctgcggatc gtttgctcag gcaggcagcc      240
gcctccggcg acacaaacag cgtgaagcgt ctggcgatag ccatggcccg caacagtact      300
ccgtggcccg gcatgaagtc tttgctggac tccatcaaca cggcggacag caagcaggcc      360
actcagctag ccgaggtata cgaaaccctg ctgagcgtgt cctccgacta cgcgcatcag      420
ctagtcggta cgacggccaa agccaagtac gaccgctacc tgcgggagac tcggtattgg      480
ggtgccgatc cggcccaggc atgggcgaag gtgcaggcgg ccgaggctgt cgatccgtcg      540
atcctgagca agcaggttgc cgatgtgtgg cgacgaaggg agaaggacat tcccaccgac      600
```

```
ttcgacgact cccattggta caaccccgtc accagggaca cgaagattca gaacctctcc      660
ctggtcaagt ccgaggtgct gcgcaccatg accgagctga tggccgaggg ccagtacgcc      720
gatgagccct ccgcagtctt tgacgccgcc tgggaaaaat tcaaaggcag ccacgtccgc      780
gtcgggaacc aatacgtctc cactttcggc accaccgagc acgtcgagcc caaacggcc      840 aaggccatga cggactacag cgtgtccttc aagaaccagc tggtccgcga agggcgccta     900
ggcgaggacg acgagctttg gttccggccc gacccgaaca ctccgggcaa gtggacggcg     960
tatgaatcca tcggaggcga gcccttccca atctcgcgcc cgggaggcgg tgttgagcag    1020
gtgaatccga acctcattcg acgccaccac gacacttggt cggcccaaga ggaccgcaag    1080
aaagccgtgt acgagcaggc tttcaatcag ggcggcctag ccggcctttt cagcccccac    1140
gaccgcgacg cggtgaacaa gaagttggac gaactgatgg acgccgacac ggttccgcac    1200
gcctcctggc acgcaaccaa tctcgatggg aagtcctttg aaatctctcg ggaacagcag    1260
gcggactatc agaagctgaa gggggtgaag gaggtcgtga acgacccaca gtacgccccg    1320
caggacttca tcgacttcat ccactccaac accgctaa                            1359

<210> SEQ ID NO 5
<211> LENGTH: 969
<212> TYPE: DNA
<213> ORGANISM: Dyella-like bacterium

<400> SEQUENCE: 5 atgagcgta gggtcggtcg caggggtgaa ggatcaggtt ccgggcaagc cgggaatcaa      60
catggagtgg ggcggggggt tatggcgcca aagaaggtaa tgttcgaagc ggggacagcg     120
gcggccgagg tgtggtcatg tatgccgtac cgctgggggc gatcaattgc gtcctctctg     180
ggcatgtttt tcaaagtgcg cactcatctc ggagtggccg tcgctgcatg gttgtgcacg     240
gcatctgccg gcgcggtcac catcaaaacg gtcgtcaatg ccgattcttc catgtgcggg    300
cagctgctca agatggtcga ggtcgccggc gtcccgcaga tgaccgatga gcagttgtgc    360
gacttccggt ttgcgaggct gccacccctcg atgactgagg gattcacctt tccgcagtgg    420
aaggaattgg ccgtggctga tgcacctggg atgtacgtgc aaatgattac ggcgaacaga    480
gcacctcatg cgccttacgg tcttcctgat ctctcctcgc gacgtgaagc ggtgaatcaa    540
gcgatgcatg agcacaattt ggctttctac aaaacaatac ttccagtgag tgagttcaag    600
tttgactata agacgtcgtc agtaactacg gtaagtaagc gagacctgac cttcgtgtca    660
atggatataa gacattgctc gaaacttcct tacaaagacc ttatagcttt tccatttat    720 gcagcctttg cggggaccga tttgaaaaat ccggtaccga cagattccat aatgagtggt    780
gatcagatgc ttggtggag aggaaataga cttgtccgaa taaacgtttc ttatcactgg    840
gtaacgatag gctctaggcc gcccggaatt gttgtggatt tagagaatct ctggtggcac    900
ccagaggaaa gaaagcttga tgctgcgata acgggtggca cccactgcag cttcagtatt    960
gataaataa                                                            969

<210> SEQ ID NO 6
<211> LENGTH: 579
<212> TYPE: DNA
<213> ORGANISM: Dyella-like bacterium

<400> SEQUENCE: 6
atgagccatg aattccgagc aaggctccga gccgcacgaa tcgttcgtcc attaacatca       60
```

```
tgggagcgat acggccctat agccgcatgg atagcggtgg cgctcgcaat ttcgattgct    120
gtacttgttt ggggcgcaga cgagtatcgt tggatagcca tcgctccggc tacgttagga    180
gctttcgctg tcatccaggg actcaagcga aggaaaccca aagaatttag caaagaaggc    240
ctagcgcagg cctctgcgac taggcaatta gaccgcgaaa aacttggcac agatgtacga    300
tcattcctga agggttggct aggcaggctt ctagtgtctg gagctatcgt ggggagctgc    360
tacttgtatg ccaagcaagg ccagatcaca aaggacgagg gattttttcct cttgctgctc    420 tgcatcggtg cggcgatctg gcatggcaa acatcgctcg cattacttgc gtgcggtgtc     480
ttgtggtggc taaccactct tgattggcac ctatccacgc caaccgcggt catcgtcggc    540
gcccttatca ttgctgccgc aatacggagc aaacattaa                           579

<210> SEQ ID NO 7
<211> LENGTH: 300
<212> TYPE: DNA
<213> ORGANISM: Dyella-like bacterium

<400> SEQUENCE: 7
atgttcagct tgacctggga agaggtgtgg cgcgcgcgca gcaccgccgc catgaggcac     60
gagtcgccgg ccgccaccgg gcccgccccg gcaccggctt cgacgaacaa gaccgcaccg    120
gcggcccgcc cccggcgcga tggaacgacg gcggcgtcgc accgccacca tcccaaagcg    180
gccgccgcgc acgccccacg cggccggca cggcggcgct ccgccgaacg gaccgacacc     240
ccacccgcac cggcatcgac cgtaacgcat cgccgcgcga tgcgcgcccc cggccgctga    300

<210> SEQ ID NO 8
<211> LENGTH: 663
<212> TYPE: DNA
<213> ORGANISM: Dyella-like bacterium

<400> SEQUENCE: 8
atgcccttgc cggtggaaac acggataaaa cctacgcaga catcgcttgc cacggtgcag     60
ccggatcggg ctcaccggtt ggatcgcgtg actttcttcc atgtgcccga tgctttgctt    120
cttgctccat cgcaggcatg gcgcaggtgt cgccactacg ctccgcaacg catcccggcg    180
gagcctcaca aaggtccaga cgcgccgttg cgcatccatc cgtggaatcc ggcccgctta    240
cgttcacggc atgcgcgcga tgcgcatcgc cgtacgcctt ggcaacggcc ggtgggggt    300 acgctttggg gccaggacgg gcttggtgcg acgagggcta tcccggccct agccgttcgc    360
ggctgggccg gtggcccga agctgccggg cgaggccgtg cgcctcgagc ccgccagcgg    420
ggtcgcctgc gcgaacgcag gcagtccaag ggaagaatag gcaaagcgct tcatcggaaa    480
ctccctttcg acgaacgagc tgcaacgtcc acttgccatg ccgctccatg ctgcggcccc    540
ctgtgcgttc ggcggaatgc gcttgggaga acgccgaacg gtgctgcttg catcgatgcg    600
atgccgggcc atgagccatg gccggtgcgg attttgagca cgaaatgcag cggcagtatg    660
tga                                                                  663

<210> SEQ ID NO 9
<211> LENGTH: 324
<212> TYPE: DNA
<213> ORGANISM: Dyella-like bacterium

<400> SEQUENCE: 9
atgcctcgcc ctcaccaccg cttgaactgg ctctacgacg aacgcacaca gacgttctca     60
accccggccg gcactgtctc gcttcgcgaa ctcgcgcagt gccgcgtcgc cctcaacaac    120
```

| | |
|---|---|
| ggacacctcg acctaaccgg accctgggcc ggctggcgcc tgcgcgccga cgtgatgccg | 180 |
| cagttcctaa ggtggcttga cgagtgcgcg cgacgcgacg ccgccgcctg cgggctgaac | 240 |
| caccggccgc cgcgccggct gttcgtcgtc actaccgaag cggccgatcc gcaagcacgc | 300 |
| cggcgcaatg aaccgggcga ctga | 324 |

<210> SEQ ID NO 10
<211> LENGTH: 1302
<212> TYPE: DNA
<213> ORGANISM: Dyella-like bacterium

<400> SEQUENCE: 10

| | |
|---|---|
| atgctccggg ccgccgagcg gccggcgcag gcgctcgcgc tcggccggcg ggaacagcgc | 60 |
| cggctgcgcc gcggcgatca gcgccaggcg cgccatcagc gcggcggcac gcgggtcgcc | 120 |
| gacgaaggga taggcggcca gcagcatttg cttggcctcg gcgcgaccgc ccgcctgcag | 180 |
| cagccggtag ctgagcggat cgagcagccg ctgcccgccg ggcgcggcca gcatggccgc | 240 |
| cgcctcgcgc gcggcctccc cgcggcggcc gtcctgcagg gcgaggtcga agcgcgtctc | 300 |
| gcggtagctg tcgggcggca gccgcgccag caggcgctgc gcggtggcac gatcgtcgcg | 360 |
| cgccagcgcg gcgggcagcg ccagccgcgc ctgcaacacg cggttgcgcg gataggccgg | 420 |
| ccggtagccg gccagcaggg ccggccgctc gcgcgcggta cgggcgagca ggtagagcca | 480 |
| ggcctgttcg tcctgctcct gcgcgaaggc gggcggcgcg ccgtgggcga ggtagctgcc | 540 |
| cagttcgtcc aggtcgccgc ggtcggccca ggcctgggcc agcgccagcc gcagcggcgg | 600 |
| cgcgtccagc ccgccgcggg cctgcaagcg ttcggcctcg ttcagctgcc cctgctgcaa | 660 |
| cagcagggcg aaccattgcc cgcgctcgcc gccctccagc tggcccgcct ggtcgagcac | 720 |
| gacgaactgc tgcgtggcgc gcgccgtgtc gcccaggaat accgcccgct gtgccagcgc | 780 |
| gcggcgcagc gccacgccgg cctcgctgtg cgcgaaggcc ggcgcgtcca gctcggcctg | 840 |
| ggcggcggcc agttcgccgc gatgcagggc ggcatagccg cgctgggccc ggcaggcgtc | 900 |
| gctgccgtcg cggcggcagt cgggcgcggg cgccaccggc gccgtcgggg cgaaggcctg | 960 |
| catcgccgcg cgcagccgcg ggtcctgcgg ggtcgcgcgt cgctgcgctt cgagcaactg | 1020 |
| gcgcgcgagg tccggatgac cgaagcgccg ataggcctcg gcaaggtcca gcgcggtctc | 1080 |
| cgcgctgtcc ggcgccagcg cgcgcgcgcg gcggaattcg tcgatggccg tctgctcgtc | 1140 |
| gccggcctgc atcgccgcgt gcgcgcgctg ctggtgcggg tagagcagga agcggcggta | 1200 |
| cgcgcccacc tcgccctcgc cggttccggc gggcggctgt tgcgcgtgga ggggcgcggc | 1260 |
| gagcgccacg gtcatcagcg ccagcgcgca gcattccggt ag | 1302 |

<210> SEQ ID NO 11
<211> LENGTH: 429
<212> TYPE: DNA
<213> ORGANISM: Dyella-like bacterium

<400> SEQUENCE: 11

| | |
|---|---|
| atgcgttcca tatggatggg tggcctgata gcgccctttgg tggctccgct aatattttc | 60 |
| ttcgccatta tggtcatggc tatatctaag gatgggtggg gtgcaggaat gcatgactgg | 120 |
| gctcaagggc tggggttagt tgccatcatt accttaccga ttagttacct ggccacatgg | 180 |
| tgttttgggg tgccatatat ttattggctt cgctcgatat ctcgcctatc aagatataat | 240 |
| gtgtgctttg ggtctcttat tattggtgtc ttgagtgcat gggccttcca gttgattatc | 300 |

```
aaggttggtc gacttgatgc tctggcattg cttcttgggg caattattgg catggcgctg    360
agtctcgctg tggcacttgt cttttgttgg gttgctagga ttccacgacc gacgtccccc    420
cacttttga                                                            429
```

```
<210> SEQ ID NO 12
<211> LENGTH: 333
<212> TYPE: DNA
<213> ORGANISM: Dyella-like bacterium

<400> SEQUENCE: 12
atggcgagat ggcgcatgag gattctccct ctcgtatcga ggaggatcat ccgcgtacgc     60
ggccgcgccg gcaaccgggc ggccgcggca cgcaccgggc gacaccgccg cttcgtgccg    120
gccttccgca agcccccgcc cctcacctcg atcctttccc cggcggggag aggaggcaga    180
gcgttgcgcc tcgtattcat cgcgaacgac tccttctccg ctggaagaga aagcaaagcg    240
cagcacccca cgctcaccgc gaaccgcgcc ctttccccccg cgggcctgat tagcgtcgca    300
tctcagttgc ccctcaccgt cattccggcg taa                                 333
```

```
<210> SEQ ID NO 13
<211> LENGTH: 972
<212> TYPE: DNA
<213> ORGANISM: Dyella-like bacterium

<400> SEQUENCE: 13
gtggacgatg aatgcggcct cgttcaccaa cgccggcgcg gtggaagcca agcaggccct     60
gagcctgagc agcggcggcg acatcagcaa cacgggcacc ttgcaggccg acaacggcga    120
cctcagcctg cgtggcggcg gcagcctggg caaccgcggc acgctgagcg ccaccggcaa    180
cctcacactg agcaccggcc gggccctgag cagcacgggc caggccgtcg ccaccggcaa    240
cgtgagcctg gaaggcgccg acctggccac cggcggcgtg gtgcaggccg gcaggccttt    300
gaacctgcgc gcgcacggcg cgctgaccaa tgccggcaag ctgcacgcgc tgggcggtgg    360
ctggacggcg caggtcgacg gcagtttcgg caaccagggc acgggcgacc tctacggcag    420
cggcgacgtc gtgctcaagg ccgcctcgct gacccaggcc ggcacgctgg aggcgacgca    480
ctcggccacg ctcggcatcg gcggtgcgct cgccaatacc ggcgtggtgc aagccgatca    540
gggcgacatc gcgctcacgg caggaagcct cgacaatgca ggtaccttca gcgccacgcg    600
cgcgctcggt gccaccgtag gcacccaggc gagcaacagc ggcacgttgg tgagtggtgc    660 agggcttttcc cttgcggccg gccatctgat caacgccgcc accggccaag ttcagagcgg    720
caccgatctt cacgtgcagg cggccgcgct ggacaacggc ggcagcctgt acgccaaggg    780
cagcggctat gccggcggag gagatttcaa caacctcgct ggcgcgcaat ggctcgcgga    840
cggtgcgttg acgttggaca acaccggcgc agtgagcaat gccggcgtgc tgcaggccgg    900
gagcgatctt gccctggggc atgccgcctc gctctccaac gtggccggcg cgacggtcta    960
tgcgggtcat ga                                                        972
```

```
<210> SEQ ID NO 14
<211> LENGTH: 453
<212> TYPE: DNA
<213> ORGANISM: Dyella-like bacterium

<400> SEQUENCE: 14
atgaggaagc ttgcttttgc tgcttttcta gctcttgtat gtgcagcgca tgcgaacgag     60
ttgggccacc atttctactc ggtgacctt aagaaggacg gcgcgattgt gggttcttgg    120
```

```
cctgttgctc tcgattcgcc tggcgcgacc atgaatggcc cggtagaaga tattggttat      180
gcggaatgtg ttcctggggg aatgaagaca gcctttgcga cagttgggtg ggttgtgatt      240
gctaaccgca cgagcggcga caagatcacg ttcgaggttc gagcatctga actcaccatc      300
tcgaaaaatg atcttctgaa gcagtgcttc aacggcgcac caccaatgcg ggttgcgcac      360
tgggagccgg tgacgctgga gcttaagaag ggcgaggctt acacatggcc gaccagtgaa      420
gggtattcag cagtcgtcga acgaactgac taa                                   453
```

<210> SEQ ID NO 15
<211> LENGTH: 1465
<212> TYPE: DNA
<213> ORGANISM: Dyella ginsengisoli

<400> SEQUENCE: 15

```
attgacgctg gcggcatgct taacacatgc aagtcgaacg gcagcacagc agagcttgct       60
ctgtgggtgg cgagtggcgg acgggtgagt aatgcatcgg gacctaccca gacgtggggg      120
ataacgtagg gaaacttacg ctaataccgc atacgtccta cgggagaaag cagggaccct      180
tcgggccttg cgcggttgga cggaccgatg ttcgattagc ttgttggtga ggtaatggct      240
caccaaggcg acgatcgata gctggtctga gaggatgatc agccacactg ggactgagac      300
acggcccaga ctcctacggg aggcagcagt ggggaatatt ggacaatggg cgcaagcctg      360
atccagcaat gccgcgtgtg tgaagaaggc cttcgggttg taaagcactt ttatcaggag      420
cgaaacgctg tcggctaata cccggcggaa ctgacggtac ctgaggaata agcaccggct      480
aacttcgtgc cagcagccgc ggtaatacga agggtgcaag cgttaatcgg aattactggg      540
gcgtaaagcg tgcgtaggcg gtttgttaag tctgctgtga atccccgggg ctcaacctgg      600
gaatggcagt ggatactggc aagctagagt gtgtcagagg gtggtggaat tcccggtgta      660
gcggtgaaat gcgtagagat cgggaggaac atcagtggcg aaggcggcca cctgggacaa      720
cactgacgct gaggcacgaa agcgtgggga gcaaacagga ttagataccc tggtagtcca      780
cgccctaaac gatgcgaact ggatgttggt ctcaactcgg agatcagtgt cgaagctaac      840
gcgttaagtt cgccgcctgg ggagtacggt cgcaagacta aaactcaaag gaattgacgg      900
gggcccgcac aagcggtgga gtatgtggtt taattcgatg caacgcgaag aaccttacct      960
ggccttgaca tgtccggaat cctgcagaga tgcgggagtg ccttcgggaa tcggaacaca     1020
ggtgctgcat ggctgtcgtc agctcgtgtc gtgagatgtt gggttaagtc ccgcaacgag     1080
cgcaacccct gtccttagtt gccagcacgt aatggtggga actctaagga gactgccggt     1140
gacaaaccgg aggaaggtgg ggatgacgtc aagtcatcat ggcccttacg gccagggcta     1200
cacacgtact acaatggtcg gtacagaggg ttgcaatacc gcgaggtgga gccaatccca     1260
gaaagccgat cccagtccgg attggagtct gcaactcgac tccatgaagt cggaatcgct     1320
agtaatcgca gatcagctat gctgcggtga atacgttccc gggccttgta cacaccgccc     1380
gtcacaccat gggagtgagt tgctccagaa gccgttagtc taaccgcaag ggggacgacg     1440
accacggagt ggttcatgac tgggg                                           1465
```

<210> SEQ ID NO 16
<211> LENGTH: 21
<212> TYPE: DNA
<213> ORGANISM: Artificial sequence
<220> FEATURE:
<223> OTHER INFORMATION: Synthetic -continued

```
<400> SEQUENCE: 16
gttcccgggc cttgtacaca c                                                21

<210> SEQ ID NO 17
<211> LENGTH: 21
<212> TYPE: DNA
<213> ORGANISM: Artificial sequence
<220> FEATURE:
<223> OTHER INFORMATION: Synthetic

<400> SEQUENCE: 17
ggttcttttc acctttccct c                                                21

<210> SEQ ID NO 18
<211> LENGTH: 20
<212> TYPE: DNA
<213> ORGANISM: Artificial sequence
<220> FEATURE:
<223> OTHER INFORMATION: Synthetic

<400> SEQUENCE: 18
ctctgtgggt ggcgagtggc                                                  20

<210> SEQ ID NO 19
<211> LENGTH: 18
<212> TYPE: DNA
<213> ORGANISM: Artificial sequence
<220> FEATURE:
<223> OTHER INFORMATION: Synthetic

<400> SEQUENCE: 19
accgtcagtt ccgccggg                                                    18

<210> SEQ ID NO 20
<211> LENGTH: 20
<212> TYPE: DNA
<213> ORGANISM: Artificial sequence
<220> FEATURE:
<223> OTHER INFORMATION: Synthetic

<400> SEQUENCE: 20
gccactcgcc acccacagag                                                  20

<210> SEQ ID NO 21
<211> LENGTH: 18
<212> TYPE: DNA
<213> ORGANISM: Artificial sequence
<220> FEATURE:
<223> OTHER INFORMATION: Synthetic

<400> SEQUENCE: 21
gctgcctccc gtaggagt                                                    18
```